US011369795B2

(12) United States Patent
Corndorf et al.

(10) Patent No.: US 11,369,795 B2
(45) Date of Patent: Jun. 28, 2022

(54) METHOD AND APPARATUS FOR CHARGE BALANCING DURING DELIVERY OF ELECTRICAL STIMULATION

(71) Applicant: Medtronic, Inc., Minneapolis, MN (US)

(72) Inventors: Eric D. Corndorf, Minneapolis, MN (US); Robert T. Sawchuk, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

(21) Appl. No.: 15/964,355

(22) Filed: Apr. 27, 2018

(65) Prior Publication Data

US 2019/0329041 A1 Oct. 31, 2019

(51) Int. Cl.
*A61N 1/36* (2006.01)
*A61N 1/362* (2006.01)
*A61N 1/37* (2006.01)

(52) U.S. Cl.
CPC ....... *A61N 1/36167* (2013.01); *A61N 1/3624* (2013.01); *A61N 1/36125* (2013.01); *A61N 1/36153* (2013.01); *A61N 1/3627* (2013.01); *A61N 1/36139* (2013.01); *A61N 1/3706* (2013.01)

(58) Field of Classification Search
CPC ............ A61N 1/36167; A61N 1/36125; A61N 1/36153; A61N 1/3624; A61N 1/36139; A61N 1/3627; A61N 1/3706
See application file for complete search history.

(56) References Cited

U.S. PATENT DOCUMENTS

| 5,083,562 | A | 1/1992 | de Coriolis et al. |
| 5,601,608 | A | 2/1997 | Mouchawar |
| 5,718,718 | A | 2/1998 | Kroll et al. |
| 6,671,546 | B2 | 12/2003 | Cansell et al. |
| 8,195,291 | B2 | 6/2012 | Norton et al. |
| 8,340,762 | B2 | 12/2012 | Vonk et al. |
| 9,656,076 | B2 | 5/2017 | Trier et al. |
| 9,855,414 | B2 | 1/2018 | Marshall et al. |
| 2009/0270943 | A1* | 10/2009 | Maschino ............ A61N 1/0551 607/45 |
| 2012/0010679 | A1 | 1/2012 | Edvinsson |
| 2014/0005753 | A1 | 1/2014 | Carbunaru |
| 2014/0107720 | A1* | 4/2014 | Bornzin ............. A61N 1/36167 607/9 |

(Continued)

OTHER PUBLICATIONS (PCT/US2019/029086) PCT Notification of Transmittal of the International Search Report and the Written Opinion of the International Searching Authority, dated Sep. 9, 2019, 12 pages.

(Continued)

*Primary Examiner* — Catherine M Voorhees
*Assistant Examiner* — Roland Dinga

(57) ABSTRACT

A medical device is configured to deliver a series of electrical stimulation pulses including opposing polarity pulses. The medical device delivers a charge balancing pulse by modifying every nth pulse of the electrical stimulation pulses to reduce a net charge delivered over the series of electrical stimulation pulses. In some examples, the medical device may be an implantable medical device that is coupled to an extra-cardiovascular lead for delivering the cardiac pacing pulses.

31 Claims, 11 Drawing Sheets

(56) References Cited

U.S. PATENT DOCUMENTS

| | | |
|---|---|---|
| 2014/0277267 A1 | 9/2014 | Vansickle et al. |
| 2015/0306375 A1 | 10/2015 | Marshall et al. |
| 2015/0360041 A1 | 12/2015 | Stahmann et al. |
| 2016/0158567 A1 | 6/2016 | Marshall et al. |
| 2016/0228708 A1 | 8/2016 | Ternes et al. |
| 2017/0157399 A1 | 6/2017 | Anderson et al. |
| 2017/0157413 A1* | 6/2017 | Anderson ............ A61N 1/3621 |
| 2017/0259065 A1 | 9/2017 | Baru et al. |

OTHER PUBLICATIONS

Grinberg et al., "Charge Balanced Cardiac Pacing From High Voltage Circuitry of an Extra-Cardiovascular Implantable Cardioverter Defibrillator System", U.S. Appl. No. 15/425,169, filed Feb. 6, 2017, 73 pages.

* cited by examiner

450

| Z | HV | LV |
|---|----|----|
| A-B | N1 | N4 |
| B-C | N2 | N5 |
| C-D | N3 | N6 |

FIG. 10

METHOD AND APPARATUS FOR CHARGE BALANCING DURING DELIVERY OF ELECTRICAL STIMULATION

TECHNICAL FIELD

This disclosure relates to a medical device and method for charge balancing electrical stimulation pulses delivered to a patient, such as cardiac pacing pulses.

BACKGROUND

A variety of medical devices exist for delivering an electrical stimulation therapy, monitoring a physiological condition of a patient or a combination thereof. Some of these medical devices include implantable medical devices (IMDs) that deliver electrical stimulation pulses using implanted electrodes. In some examples, IMDs may employ one or more elongated electrical leads carrying stimulation electrodes, sensing electrodes, and/or other sensors. IMDs may deliver therapy to or monitor conditions of a variety of organs, nerves, muscle or tissue, such as the heart, brain, stomach, spinal cord, pelvic floor, or the like. Implantable medical electrical leads may be configured to position electrodes or other sensors at desired locations for delivery of electrical stimulation or sensing of physiological conditions. For example, electrodes or sensors may be carried along a distal portion of a lead that is extended subcutaneously, submuscularly, intra-thoracically, intra-abdominally, intra-cranially, or transvenously. A proximal portion of the lead may be coupled to the housing of the IMD, providing electrical connection to circuitry contained within the housing such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical pulses to the heart to address abnormal cardiac rhythms.

IMDs capable of delivering electrical pulses for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, a pacemaker or ICD may deliver pacing pulses to the heart upon detecting bradycardia or tachycardia. An ICD may deliver high voltage cardioversion or defibrillation shocks to the heart upon detecting fast ventricular tachycardia or fibrillation.

SUMMARY

The techniques of this disclosure generally relate to a medical device and method for charge balancing electrical stimulation pulses delivered to a patient's body tissue, such as cardiac pacing pulses or neurostimulation pulses, via one or more electrodes. Electrode corrosion can occur when electrical stimulation pulses delivered by the electrodes deliver a net electrical charge that accumulates over time. This effect can be minimized by charge balancing the electrical stimulation pulses to thereby reduce or eliminate the net charge that accumulates due to the delivered pulses. A medical device operating according to the techniques disclosed herein controls the polarity, amplitude and pulse width of each electrical stimulation pulse in order to provide charge balancing over a series of electrical stimulation pulses.

In one example, the disclosure provides a medical device having a therapy delivery circuit and a control circuit. The therapy delivery circuit is configured to generate and deliver electrical stimulation pulses via electrodes coupled to the therapy delivery circuit. The control circuit is coupled to the therapy delivery circuit and is configured to control the therapy delivery circuit to deliver electrical stimulation pulses comprising opposing polarity electrical stimulation pulses and deliver a charge balancing pulse by modifying every nth pulse of the electrical stimulation pulses. The charge balancing pulse is delivered to reduce a net charge delivered over the electrical stimulation pulses.

In another example, the disclosure provides a method performed by a medical device. The method includes delivering electrical stimulation pulses comprising opposing polarity electrical stimulation pulses and delivering a charge balancing pulse by modifying every nth pulse of the electrical stimulation pulses. The charge balancing pulse is delivered to reduce a net charge delivered over the electrical stimulation pulses.

In yet another example, the disclosure provides a non-transitory, computer-readable medium storing a set of instructions which when executed by a control circuit of a medical device, cause the medical device to deliver electrical stimulation pulses comprising opposing polarity electrical stimulation pulses and deliver a charge balancing pulse by modifying every nth pulse of the electrical stimulation pulses. The charge balancing pulse is delivered to reduce a net charge delivered over the electrical stimulation pulses.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 10 is a conceptual diagram of one example of a lookup table that may be stored in the memory of an ICD.

DETAILED DESCRIPTION

Figure 1A:
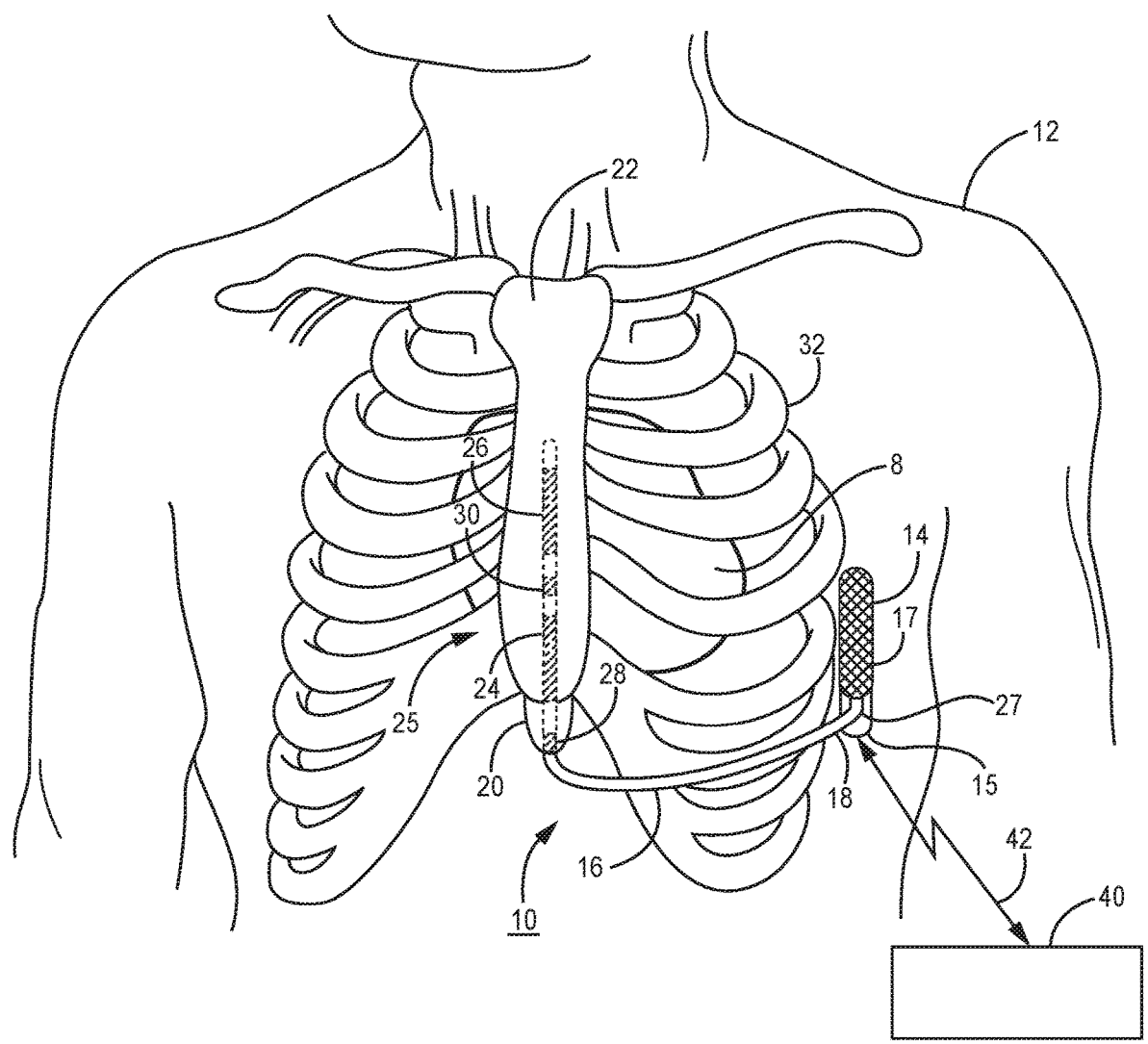
FIGS. 1A and 1B are conceptual diagrams of an extra-cardiovascular ICD system according to one example.

In general, this disclosure describes techniques for charge balancing electrical stimulation pulses delivered to a patient. For example, the techniques may be particularly useful in the delivery of cardiac pacing pulses but may be applied in the delivery of neurostimulation pulses or any other electrical stimulation pulses delivered to a patient's body tissue via medical electrodes. The delivered electrical stimulation pulses may be delivered for therapeutic purposes, such as cardiac pacing pulses, but may be delivered for diagnostic or testing purposes in some examples. The disclosed charge balancing techniques may be implemented in any medical device configured to deliver electrical stimulation pulses, particularly electrical stimulation pulses that are delivered repetitively over time resulting in an accumulated electrical charge at the stimulating electrode(s). In some examples, the charge balancing techniques are used during the delivery of repetitive, opposing polarity electrical stimulation pulses having an inherent imbalance between the charge delivered by a positive polarity pulse compared to the charge delivered by a negative polarity pulse.

Electrical stimulation pulses that are charge balanced are intended to deliver a net-zero or near net-zero charge over time. Electrical stimulation pulses that are charge imbalanced, meaning that a non-net zero charge accumulates at the tissue-electrode interface over time, can lead to electrode corrosion and cause polarization artifact that can interfere with sensing of cardiac electrical signals. Charge accumulation may occur when the electrical stimulation pulses are imbalanced during delivery of relatively high energy pulses (e.g., high current or voltage amplitude and/or long pulse duration) as well as relatively low energy pulses (e.g., low current or voltage amplitude and/or short pulse duration).

Relatively high pulse energy pulses are delivered for cardiac pacing when a cardiac capture threshold is high. The capture threshold is the minimum pulse energy that captures the heart, causing a non-intrinsic depolarization or evoked response. Factors that may contribute to a high cardiac capture threshold include pacing lead impedance and electrode location. For example, when the heart is being paced using electrodes carried by a non-transvenous, extra-cardiovascular lead, the cardiac capture threshold is significantly higher than the cardiac capture threshold when the heart is being paced by endocardial electrodes carried by a transvenous lead, which are in intimate contact with myocardial tissue. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but may not be in intimate contact with myocardial tissue. The charge balancing techniques disclosed herein, therefore, may be used in some examples for delivering extra-cardiovascular pacing pulses or any pacing pulses delivered using electrodes that are not in direct contact with the heart.

Even relatively low energy electrical stimulation pulses, e.g., cardiac pacing pulses delivered using endocardial or epicardial electrodes in direct contact with the heart, if imbalanced, can lead to electrode corrosion over time. Charge balancing the pacing pulses may minimize these effects. In endocardial or epicardial pacing applications, the effects of imbalanced charge delivery may be mitigated by delivering a non-therapeutic, recharge pulse having the opposite polarity of the pacing pulse during the physiological refractory period of the myocardium that follows the pacing pulse. The opposite polarity recharge pulse may not be precisely charge-equivalent to the pacing pulse but may adequately prevent electrode corrosion since in endocardial or epicardial pacing, charge accumulation over time is small because the charge delivered during each pulse is relatively small. In extra-cardiovascular cardiac pacing systems, the pacing pulse energy delivered to capture the heart may be on the order of at least twice and even 10 to 100 times greater per pacing pulse than during endocardial pacing. For example, an endocardial pacing pulse may be up to 8.5 Volts in amplitude and up to 1.5 ms in pulse width and is more typically less than 5 Volts, e.g., 1 V, in amplitude and 0.5 ms in pulse width. An extra-cardiovascular pacing pulse, on the other hand, may be 10 to 40 Volts in amplitude and up to 8 ms in pulse width. As such, without charge balancing, the corrosive process acting on the pacing electrodes may be amplified 100 times or more during extra-cardiovascular pacing than during endocardial pacing. Because the non-therapeutic recharge pulses that may be applied in endocardial pacing applications are generally not precisely charge-equivalent to the therapeutic pacing pulses, the technique of using recharge pulses may not provide adequate charge balancing in all applications, particularly during delivery of high pulse energy electrical stimulation pulses because of the larger charge accumulation and corrosive effect over time.

One approach to providing charge balancing in high voltage, extra-cardiovascular pacing applications is to deliver therapeutic pulses having alternating polarity in order to provide charge balancing over each pair of pacing cycles. Examples of charge balanced pacing pulses delivered by a high voltage pacing circuit are generally disclosed in U.S. patent application Ser. No. 15/425,169 (Grinberg et al., filed Feb. 6, 2017), incorporated herein by reference in its entirety. However, in some systems, inherent imbalances of opposite polarity pulses may exist such that alternating therapeutic pulses may still result in a net charge accumulation over time and associated risk of electrode corrosion, especially in the high voltage pacing applications such as extra-cardiovascular pacing. For these reasons, charge balancing during relatively high voltage (or high current amplitude) pacing applications for preserving the integrity of the pacing system presents a greater challenge than during endocardial pacing applications which use much lower pacing pulse voltage (or current) amplitudes. Charge balancing techniques are disclosed herein for providing cardiac pacing by an IMD while preventing or minimizing electrode corrosion over time. These techniques may include delivering a series of cardiac pacing pulses having opposing polarities, which are alternating positive and negative polarity pulses in some examples, with every nth pacing pulse in the series being modified to balance a net charge delivered during the preceding one or more pulses in the series.

Figure 1B:
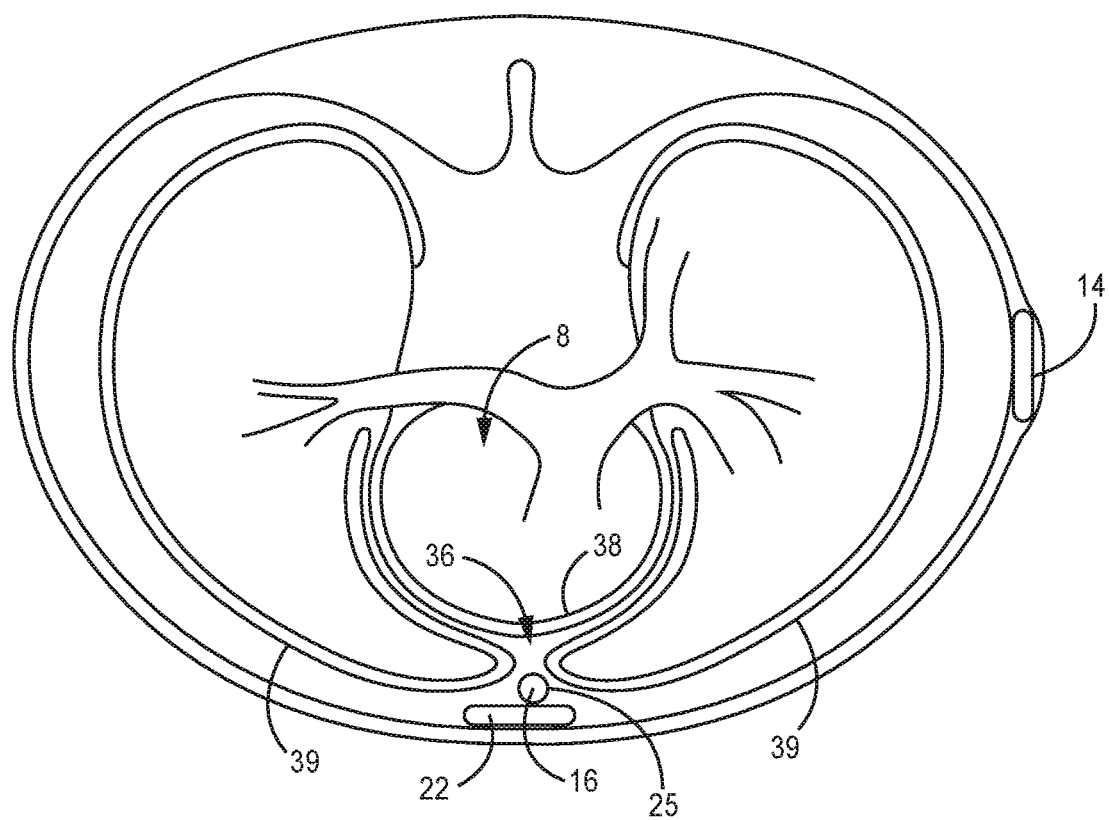

FIGS. 1A and 1B are conceptual diagrams of an extra-cardiovascular ICD system 10 according to one example. FIG. 1A is a front view of ICD system 10 implanted within patient 12. FIG. 1B is a transverse sectional view of ICD system 10 implanted within patient 12. ICD system 10 includes an ICD 14 connected to an extra-cardiovascular electrical stimulation and sensing lead 16. An "extra-cardiovascular lead" as used herein, refers to a lead that is implanted outside the heart and blood vessels of the patient's cardiovascular system. An extra-cardiovascular lead may extend subcutaneously, sub-muscularly or intra-thoracically, for example. FIGS. 1A and 1B are described in the context of an ICD system 10 capable of providing cardioversion/defibrillation (CV/DF) shocks and pacing pulses. It is contemplated that the techniques disclosed herein for providing charge balancing of cardiac pacing pulses, however, may be implemented in systems that are not configured for delivering shock therapies. The disclosed charge balancing cardiac pacing techniques may be implemented in any medical device configured to deliver cardiac pacing pulses and may also be beneficial in any medical device that delivers electrical stimulation pulses, particularly when alternating polarity pulses, or more generally a series of pulses comprising opposing polarity pulses, are delivered having an inherent imbalance in the charge delivered by the positive and negative pulses.

ICD 14 includes a housing 15 that forms a hermetic seal that protects internal components of ICD. Internal components includes pulse generating circuitry, which may include a high voltage therapy circuit, for generating high voltage CV/DF shocks and high voltage pacing pulses, and a low voltage therapy circuit, for generating relatively lower voltage pacing pulses delivered using extra-cardiovascular electrodes carried by lead 16. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering CV/DF shocks or other high voltage pulses, including cardiac pacing pulses, delivered using the high voltage therapy circuit. In other examples, housing 15 may be available for use in delivering unipolar, cardiac pacing pulses delivered using the low voltage therapy circuit in conjunction with a lead-based cathode electrode. In other instances, the housing 15 of ICD 14 may include a plurality of electrodes on an outer portion of the housing. The outer portion(s) of the housing 15 functioning as an electrode(s) may be coated with a material, such as titanium nitride to reduce post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage shock therapy pulses compared to the surface area of the pacing and sensing electrodes 28 and 30, which may be used to deliver cardiac pacing pulses that are lower in pulse energy than CV/DF shock pulses. However, electrodes 24 and 26 and housing 15 may also be utilized to provide pacing functionality, sensing functionality or both pacing and sensing functionality in addition to or instead of high voltage CV/DF shock therapy. In this sense, the use of the term "defibrillation electrode" herein should not be considered as limiting the electrodes 24 and 26 for use in only CV/DF shock therapy applications. Electrodes 24 and 26 may be used in a pacing electrode vector for delivering extra-cardiovascular pacing pulses such as but not limited to bradycardia pacing pulses, anti-tachycardia pacing (ATP) pulses, entrainment pulses for tachyarrhythmia induction, cardiac resynchronization therapy (CRT) pulses, and/or post-shock pacing pulses. Electrodes 24 and 26 may also be used in a sensing vector used to sense cardiac electrical signals and detect abnormal heart rhythms, such as ventricular tachycardia (VT) and ventricular fibrillation (VF).

Electrodes 28 and 30 are relatively smaller surface area electrodes for delivering relatively lower voltage pacing pulses and for sensing cardiac electrical signals. Electrodes 28 and 30 are referred to herein as pace/sense electrodes because they are generally configured for use in relatively lower voltage applications than defibrillation electrodes 24 and 26. Electrodes 28 and 30 may be used as either a cathode or anode for delivery of pacing pulses, including any of the examples given above, and/or sensing of cardiac electrical signals. In some instances, electrodes 28 and 30 may provide only pacing functionality, only sensing functionality or both. While electrodes 28 and 30 are generally referred to as being used for delivering relatively lower voltage pacing pulses compared to high voltage CV/DF shock pulses delivered by defibrillation electrodes 24 and 26, it is to be understood that the cardiac pacing pulses delivered using any combination of the extra-cardiovascular electrodes 24, 26, 28, 30 and housing 15 are generally higher in voltage amplitude and/or pulse width than cardiac pacing pulses delivered using endocardial or epicardial electrodes. As such, the extra-cardiovascular pacing pulses delivered by ICD system 10 are considered relatively high voltage pacing pulses (compared to pacing pulses delivered by transvenous ICD systems) and may be controlled using the charge balancing techniques disclosed herein.

In the example illustrated in FIG. 1A, electrode 28 is located proximal to defibrillation electrode 24, and electrode 30 is located between defibrillation electrodes 24 and 26. In other examples, electrodes 28 and 30 may be positioned at other locations along lead 16, which may include one or more pace/sense electrodes. Electrodes 28 and 30 are illustrated as ring electrodes, however electrodes 28 and 30 may comprise any of a number of different types of electrodes, including ring electrodes, short coil electrodes, hemispherical electrodes, directional electrodes, or the like.

Lead 16 extends subcutaneously or submuscularly over the ribcage 32 medially from the connector assembly 17 of ICD 14 toward a center of the torso of patient 12, e.g., toward xiphoid process 20 of patient 12. At a location near xiphoid process 20, lead 16 bends or turns and extends superiorly within anterior mediastinum 36 in a substernal position. Anterior mediastinum 36 (seen in FIG. 1B) may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36. A lead implanted such that the distal portion 25 is substantially within anterior mediastinum 36 may be referred to as a "substernal lead."

Figure 2A:
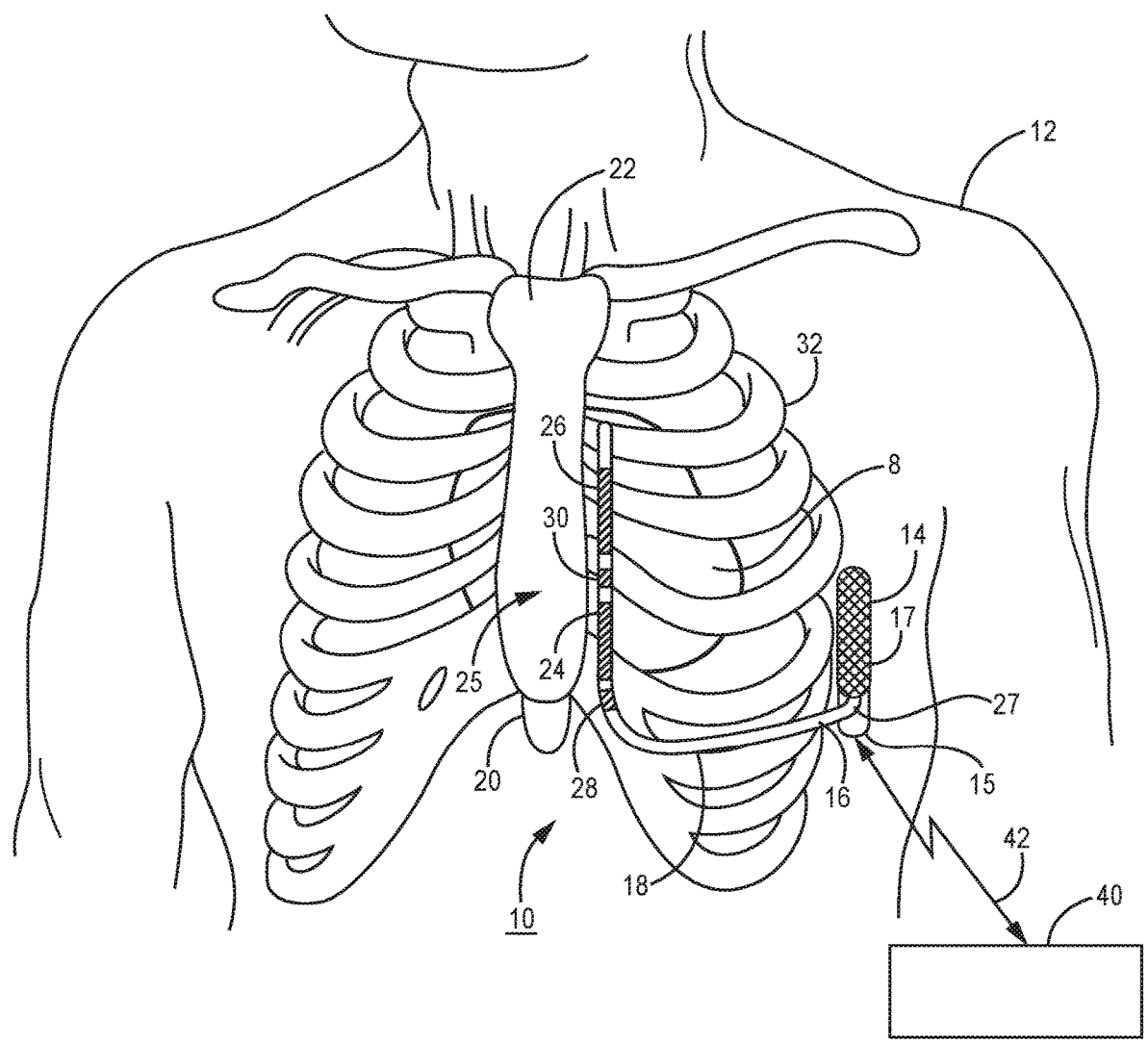
FIG. 2A is a front view and FIG. 2B is a side view of a patient implanted with an ICD system according to another example.
Figure 2B:
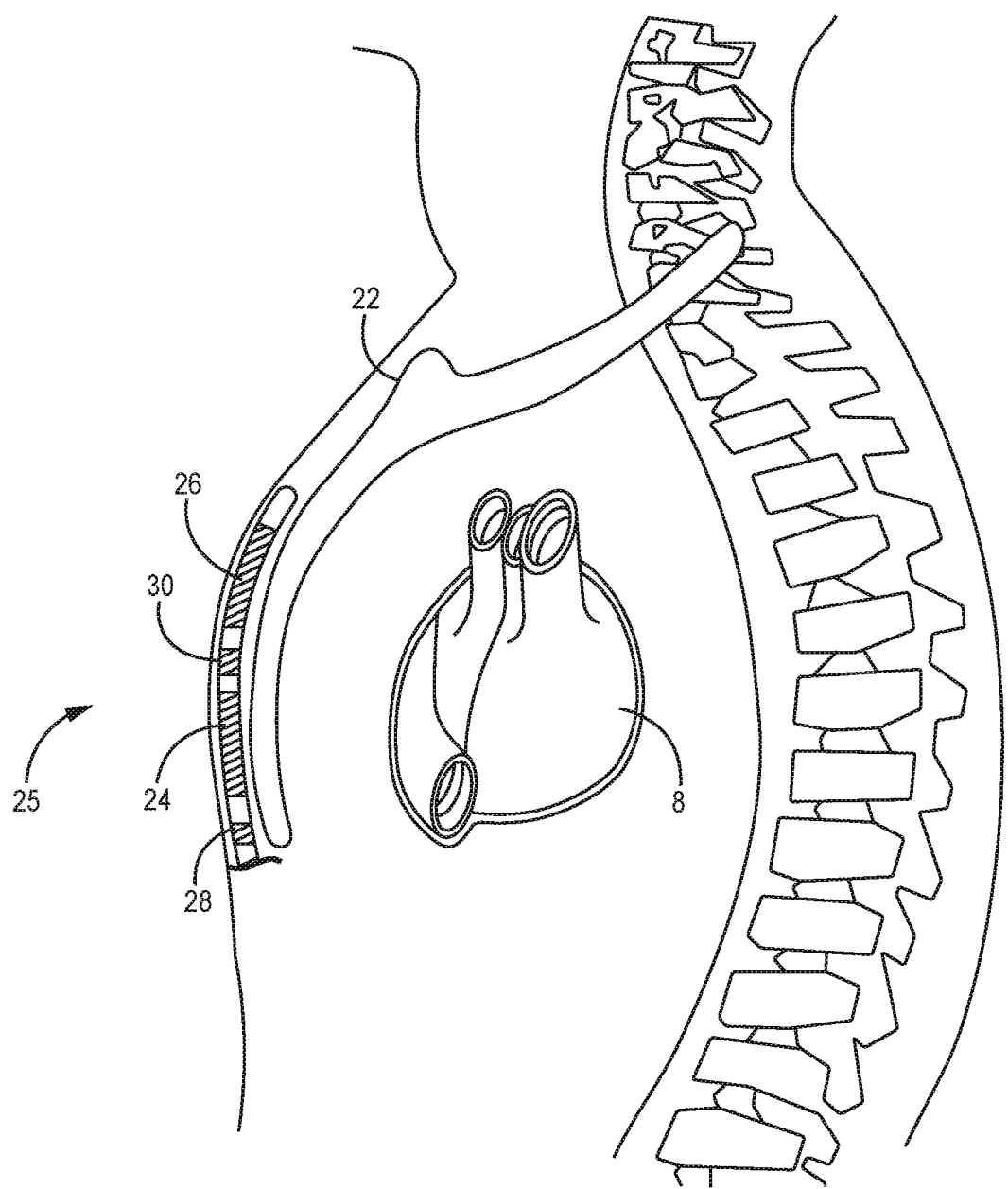

In the example illustrated in FIGS. 1A and 1B, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8. Other implant locations and lead and electrode arrangements that may be used in conjunction with the cardiac pacing techniques described herein are generally disclosed in U.S. Pat. Application Publication No. 2015/0306375 (Marshall, et al.) and U.S. Pat. No. 9,855,414 (Marshall, et al.), both of which are incorporated herein by reference in their entirety. For example, as shown in FIGS. 2A and 2B, lead 16 may extend superiorly and subcutaneously or submuscularly over the ribcage and/or sternum 22, rather than substernally. Alternatively, lead 16 may be placed along other subcutaneous or submuscular paths. The path of lead 16 may depend on the location of ICD 14, the arrangement and position of electrodes carried by the lead distal portion 25, and/or other factors.

Lead body 18 may be a flexible lead body without preformed curves or bends. In other examples an extra-cardiovascular lead including one or more defibrillation electrodes and/or one or more pacing and sensing electrodes may be carried by a lead body having one or more preformed curves or bends or a serpentine, undulating or zig-zagging distal portion of the lead body 18. Examples of other extra-cardiovascular leads that may be implemented with the techniques described herein are generally disclosed in U.S. Pat. Application Publication No. 2016/0158567 (Marshall, et al.), incorporated herein by reference in its entirety. The techniques disclosed herein are not limited to any particular electrode arrangement or lead body design, however.

Electrical conductors (not illustrated) extend through one or more lumens of the elongated lead body 18 of lead 16 from the lead proximal end 27 to electrodes 24, 26, 28, and 30 located along the distal portion 25 of the lead body 18. The conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28 and 30 and transmit cardiac electrical signals produced by the patient's heart 8 from one or more of defibrillation electrodes 24 and 26 and/or pace/sense electrodes 28 and 30 to the sensing circuit within ICD 14.

ICD 14 may obtain cardiac electrical signals corresponding to electrical activity of heart 8 via a combination of sensing vectors that include combinations of electrodes 28 and 30. In some examples, housing 15 of ICD 14 is used in combination with one or more of electrodes 28 and/or 30 in a sensing electrode vector. ICD 14 may even obtain cardiac electrical signals using a sensing vector that includes one or both defibrillation electrodes 24 and/or 26, e.g., between electrodes 24 and 26 or between one of electrodes 24 or 26 in combination with one of electrodes 28, 30 and/or housing 15.

ICD 14 analyzes the cardiac electrical signals received from one or more of the sensing vectors to monitor for abnormal rhythms, such as bradycardia, VT and VF. ICD 14 may analyze the heart rate and/or morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30 and/or housing 15.

If ATP is not delivered or does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode).

Bradycardia pacing pulses may be delivered in response to too slow of a heart rate or asystole. ICD 14 may generate and deliver cardiac pacing pulses, such as post-shock pacing pulses or bradycardia pacing pulses using a pacing electrode vector that includes one or more of the electrodes 24, 26, 28, 30 and the housing 15 of ICD 14. The timing of pacing pulses may be controlled by a controller included in ICD 14 by setting a pacing escape interval timer or counter according to a lower pacing rate or back-up pacing interval. Bradycardia pacing, post-shock pacing, CRT, atrial-tracking ventricular pacing pulses, or any other type of pacing therapy delivered by ICD 14 may be controlled using the charge balancing techniques disclosed herein.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or selected communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver cardiac pacing pulses according to the charge balancing techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

FIG. 2A is a front view and FIG. 2B is a side view of a patient implanted with ICD system 10 with extra-cardiovascular lead 16 implanted in a different location than FIGS. 1A-1B. In some examples, extra-cardiovascular electrical stimulation therapies may be delivered using electrodes that remain outside the thoracic cavity. In the example of FIG. 2A, the distal portion 25 of lead 16 extends over ribcage 32, laterally offset from and substantially parallel to sternum 22. In other examples, lead 16 may extend over sternum 22 or may extend diagonally over a portion of sternum 22 and ribcage 32.

FIGS. 1A-2B are illustrative in nature and should not be considered limiting of the practice of the techniques disclosed herein. For instance, ICD 14 is shown implanted subcutaneously on the left side of patient 12 along the ribcage 32. ICD 14 may, in other instances, be implanted between the left posterior axillary line and the left anterior axillary line of patient 12. ICD 14 may be implanted at other subcutaneous or submuscular locations in patient 12 such as in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well and include other electrode and lead body configurations.

Figure 3:
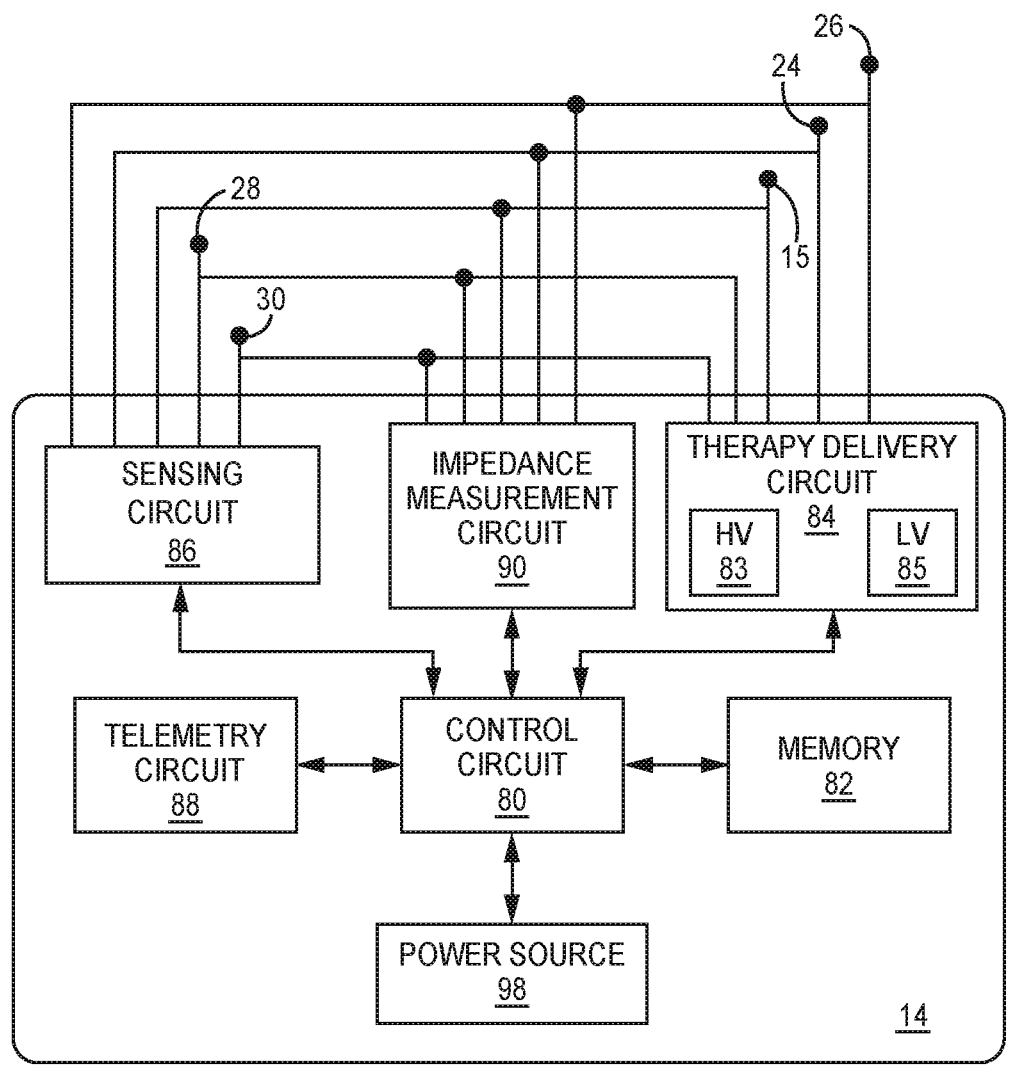
FIG. 3 is a schematic diagram of an ICD according to one example.

FIG. 3 is a schematic diagram of ICD 14 according to one example. The electronic circuitry enclosed within housing 15 (shown schematically as a can electrode in FIG. 3) includes software, firmware and hardware that cooperatively monitor one or more cardiac electrical signals, determine when a pacing therapy is necessary, and deliver prescribed pacing therapies as needed. The software, firmware and hardware are also configured to determine when a CV/DF shock is necessary, and deliver prescribed CV/DF shock therapies. ICD 14 is coupled to an extra-cardiovascular lead, such as lead 16 carrying extra-cardiovascular electrodes 24, 26, 28 and 30 for delivering pacing therapies, CV/DF shock therapies and sensing cardiac electrical signals.

ICD 14 includes a control circuit 80, memory 82, therapy delivery circuit 84, cardiac electrical signal sensing circuit 86, and telemetry circuit 88. ICD 14 may include an impedance measurement circuit 90 for delivering a drive signal across a pacing electrode vector and measuring a resulting voltage for determining an electrical impedance of the pacing electrode vector.

A power source 98 provides power to the circuitry of ICD 14, including each of the circuits 80, 82, 84, 86, 88, 90 as needed. Power source 98 may include one or more energy storage devices, such as one or more rechargeable or non-rechargeable batteries. The connections between power source 98 and each of the other circuits 80, 82, 84, 86 and 88 are to be understood from the general block diagram of FIG. 3, but are not shown for the sake of clarity. For example, power source 98 is coupled to low voltage (LV) and high voltage (HV) charging circuits included in therapy delivery circuit 84 for charging LV and HV capacitors, respectively, or other energy storage devices included in therapy delivery circuit 84 for producing electrical stimulation pulses.

The functional blocks shown in FIG. 3 represent example functionality included in ICD 14. ICD 14 may include more or fewer components than illustrated in FIG. 3. ICD 14 may include any discrete and/or integrated electronic circuit components that implement analog and/or digital circuits capable of producing the functions attributed to ICD 14 herein, which may include one or more of an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD circuits to perform various functions attributed to ICD 14 or those ICD circuits. The non-transitory computer-readable media storing the instructions may include any of the media listed above.

Functionality attributed to ICD 14 may be performed by separate hardware, firmware or software components, or integrated within common hardware, firmware or software components. For example, cardiac pacing operations may be performed by therapy delivery circuit 84 under the control of control circuit 80 and may include operations implemented in a processor executing instructions stored in memory 82.

Control circuit 80 communicates with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and electrical sensing circuit 86 are each electrically coupled to any or all of electrodes 24, 26, 28 and 30 carried by lead 16 shown in FIGS. 1A-2B and the housing 15, which may function as a common or ground electrode or as an active can electrode for delivering CV/DF shock pulses.

Cardiac electrical signal sensing circuit 86 may be selectively coupled to electrodes 24, 26, 28 and 30 and housing 15 in order to monitor electrical activity of the patient's heart. Sensing circuit 86 may include switching circuitry for selecting which of electrodes 24, 26, 28 and 30 and housing 15 are coupled to sense amplifiers or other cardiac event detection circuitry included in sensing circuit 86. Switching circuitry may include a switch array, switch matrix, multiplexer, or any other type of switching device suitable to selectively couple sense amplifiers to selected electrodes.

The cardiac event detection circuitry within electrical sensing circuit 86 may include one or more sense amplifiers, filters, rectifiers, threshold detectors, comparators, analog-to-digital converters (ADCs), or other analog or digital components.

In some examples, electrical sensing circuit 86 includes multiple sensing channels for acquiring cardiac electrical signals from multiple sensing vectors selected from electrodes 24, 26, 28 and 30 and housing 15. Each sensing channel may be configured to amplify, filter and rectify the cardiac electrical signal received from selected electrodes coupled to the respective sensing channel to improve the signal quality for sensing cardiac events, e.g., P-waves and/or R-waves. Each sensing channel includes cardiac event detection circuitry for sensing cardiac events from the received cardiac electrical signal developed across the selected sensing electrode vector(s). For example, each sensing channel in sensing circuit 86 may include an input or pre-filter and amplifier for receiving a cardiac electrical signal from a respective sensing vector, an analog-to-digital converter, a post-amplifier and filter, and a rectifier to produce a digitized, rectified and amplified cardiac electrical signal that is passed to a cardiac event detector included in sensing circuit 86 and/or passed to control circuit 80 for performing signal analysis.

The cardiac event detector may include a sense amplifier, comparator or other circuitry for comparing the rectified cardiac electrical signal to a cardiac event sensing threshold amplitude, such as an R-wave sensing threshold amplitude, which may be an auto-adjusting threshold. Sensing circuit 86 may produce a sensed cardiac event signal in response to a sensing threshold crossing. The sensed cardiac events (or lack thereof), e.g., R-waves, are used for detecting cardiac rhythms and determining a need for therapy by control circuit 80. In some examples, cardiac electrical signals such as sensed R-waves are used to detect capture of a pacing pulse delivered by ICD 14.

Therapy delivery circuit 84 may include a low voltage (LV) therapy circuit 85 for delivering low voltage pacing pulses using an extra-cardiovascular pacing electrode vector selected from electrodes 24, 26, 28 and 30 and housing 15. LV therapy circuit 85 may be configured to deliver low voltage pacing pulses, e.g., 8 V or less or 10 V or less in pulse amplitude. One or more capacitors included in the LV therapy circuit 85 are charged to a voltage according to a programmed pacing pulse amplitude by a LV charging circuit, which may include a state machine. The LV charging circuit may charge the capacitors to a multiple of the voltage of a battery included in power source 98 without requiring a transformer. At an appropriate time, the LV therapy circuit 85 couples the holding capacitor(s) to a pacing electrode vector, e.g., via a tip or output capacitor, to deliver a pacing pulse to the heart 8. One example of a LV therapy circuit is described below in conjunction with FIG. 5.

High voltage (HV) therapy circuit 83 includes one or more high voltage capacitors. When a shockable rhythm is detected, the HV capacitor(s) is(are) charged to a shock voltage amplitude by a HV charging circuit according to the programmed shock energy. The HV charging circuit 83 may include a transformer and be a processor-controlled charging circuit that is controlled by control circuit 80. Control circuit 80 applies a signal to trigger discharge of the HV capacitor(s) upon detecting a feedback signal from therapy delivery circuit 84 that the HV capacitors have reached the shock voltage amplitude required to deliver the programmed shock energy. In this way, control circuit 80 controls operation of the HV therapy circuit 83 to deliver CV/DF shocks using defibrillation electrodes 24, 26 and/or housing 15.

HV therapy circuit 83 may be used to deliver cardiac pacing pulses in some applications. In this case, the HV capacitor(s) is(are) charged to a much lower voltage than that used for delivering shock therapies but may be higher than the maximum available pulse voltage amplitude produced by the LV therapy circuit 85. For example, the HV capacitor may be charged to 40 V or less, 30 V or less, or 20 V or less for producing extra-cardiovascular pacing pulses. In some examples, HV therapy circuit 83 is enabled to deliver cardiac pacing pulses by applying at least a minimum electrical current required to maintain switches included in HV therapy circuit 83 in a closed state as needed for coupling the HV capacitor(s) to a pacing electrode vector. Circuitry included in HV therapy circuit 83 is described in conjunction with FIG. 4 below.

Compared to pacing pulses delivered by LV therapy circuit 85, pulses delivered by HV therapy circuit 83 may have a higher voltage amplitude and/or relatively longer pulse width for delivering higher energy pacing pulses for capturing the heart. More current may be delivered using a low impedance pacing electrode vector, e.g., between electrodes 24 and 26. Longer pulse width is attainable due to a higher capacitance (and consequently higher RC time constant) of the HV capacitor(s). The LV therapy circuit 85 may be capable of producing a maximum pulse voltage amplitude of up to and including 10 V. The maximum single-pulse pacing pulse width produced by LV therapy circuit 85 may be 2 ms. In some examples, LV therapy circuit 85 may be configured to produce composite pacing pulses comprising two or more individual pulses fused in time to deliver a cumulative composite pacing pulse energy that captures the heart. Techniques for delivering composite pacing pulses are generally disclosed in U.S. Pat. Application Publication No. 2017/0157413 (Anderson, et al.) and U.S. Pat. Application Publication No. 2017/0157399 (Anderson, et al.), both incorporated herein by reference in their entirety. The composite pacing pulse width may be 4 ms or higher, for example.

The HV therapy circuit 83 may be capable of producing a pulse voltage amplitude of 10 V or more and may produce mono- or multi-phasic pulses having a relatively longer pacing pulse width, e.g., 10 ms or more, because of the higher capacitance of high voltage capacitors included in HV therapy circuit 83. A typical HV pacing pulse width may be 10 ms; however an example range of available pulse widths may be 2 ms to 20 ms. An example of a maximum voltage amplitude that may be used for delivering high voltage pacing pulses may be 40 V. When a relatively higher pacing pulse voltage amplitude is tolerable by the patient, e.g., more than 10 V, a relatively shorter pacing pulse width, e.g., 2 to 5 ms, may be used during an extra-cardiovascular pacing output configuration. However, a longer pacing pulse width may be used as needed, e.g., a 10 V, 20 ms pacing pulse, to capture the patient's heart without causing pain or discomfort.

For the sake of comparison, the HV capacitor(s) of the HV therapy circuit 83 may be charged to an effective voltage greater than 100 V for delivering a CV/DF shock. For example, two or three HV capacitors may be provided in series having an effective capacitance of 148 to 155 microfarads in HV therapy circuit 83. These series capacitors may be charged to develop 100 to 800 V for the series combination in order to deliver shocks having a pulse energy of 5 Joules or more, and more typically 20 Joules or more.

In contrast, pacing pulses delivered by the HV therapy circuit 83 may have a pulse energy less than 1 Joule and even in the milliJoule range or tenths of milliJoules range depending on the pacing electrode impedance. For instance, a pacing pulse generated by HV therapy circuit 83 having a 10 V amplitude and 20 ms pulse width delivered using a pacing electrode vector between defibrillation electrodes 24 and 26, having an impedance in the range of 20 to 200 ohms, may have a delivered energy of 5 to 7 milliJoules. When a relatively shorter pulse width is used, e.g., down to 2 ms, the pacing pulse delivered by HV therapy circuit 83 using defibrillation electrodes 24 and 26 may be as low as 1 milliJoule. Pacing pulses delivered by HV therapy circuit 83 are expected to have a pacing voltage amplitude that is less than 100 V, and typically not more than 40 V, and deliver at least 1 milliJoule but less than 1 Joule of energy. The delivered energy for a given pacing voltage amplitude will vary depending on the pulse width and pacing electrode vector impedance.

If a pace/sense electrode 28 or 30 is included in the pacing electrode vector, resulting in a relatively higher impedance, e.g., in the 400 to 1000 ohm range, the pacing pulse energy delivered may be in the range of 2 to 5 milliJoules. HV therapy circuit 83 may deliver more current via a lower impedance pacing electrode vector, e.g., between defibrillation electrodes 24 and 26, than the current delivered by LV therapy circuit 85 via a pacing electrode vector including a pace/sense electrode 28 and 30 (relatively higher impedance) even when the pacing voltage amplitude is the same.

Composite pacing pulses, delivered by the LV therapy circuit 85, having an 8 V amplitude and 8 ms pulse width may be in the range of 0.5 to 1.3 milliJoules for the range of pacing loads given in the preceding example. Extra-cardiovascular, single-pulse pacing pulses delivered by LV therapy circuit 83 that are 8V in amplitude and 2 ms in pulse width may be in the range of 0.2 to 0.3 milliJoules for pacing loads of 400 to 1000 ohms. In contrast, pacing pulses delivered using endocardial electrodes or epicardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms. As such, even though LV therapy circuit 83 is referred to herein as a "low voltage" therapy circuit, cardiac pacing delivered by LV therapy circuit 83 may still be considered a high voltage pacing application relative to very low voltage pacing applications that utilize endocardial or epicardial electrodes because LV therapy circuit 85 is configured to deliver pacing pulses via extra-cardiovascular electrodes. As will be described below, control circuit 80 may control therapy circuit 84 to deliver cardiac pacing pulses using the charge balancing techniques disclosed herein. The cardiac pacing pulses may be generated by HV therapy circuit 83 or LV therapy circuit 85.

In some instances, control circuit 80 may control impedance measurement circuit 90 to determine the impedance of a pacing electrode vector. Impedance measurement circuit 90 may be electrically coupled to the available electrodes 24, 26, 28, 30 and housing 15 for performing impedance measurements of one or more candidate pacing electrode vectors. Control circuit 80 may control impedance measurement circuit 90 to perform impedance measurements by passing a signal to impedance measurement circuit 90 to initiate an impedance measurement of a pacing electrode vector. Impedance measurement circuit 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control circuit 80.

Control circuit 80 may use impedance measurements from impedance measurement circuit 90 to control delivery of pacing pulses using the charge balancing techniques disclosed herein. For instance, the pacing vector impedance may be used in selecting how often a modified pacing pulse is injected in a series of alternating polarity pacing pulses to provide charge balancing. As described below, the pacing electrode vector impedance may be used as an input to an algorithm for selecting the modification of an nth pacing pulse in a series of alternating polarity pacing pulses or used to determine the modification of an nth pacing pulse from a lookup table stored in memory 82 based on multiple impedance ranges.

Control parameters utilized by control circuit 80 for detecting cardiac rhythms and delivering electrical stimulation therapies and tachyarrhythmia induction pulses, including charge balancing pacing pulse modifications, may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 4:
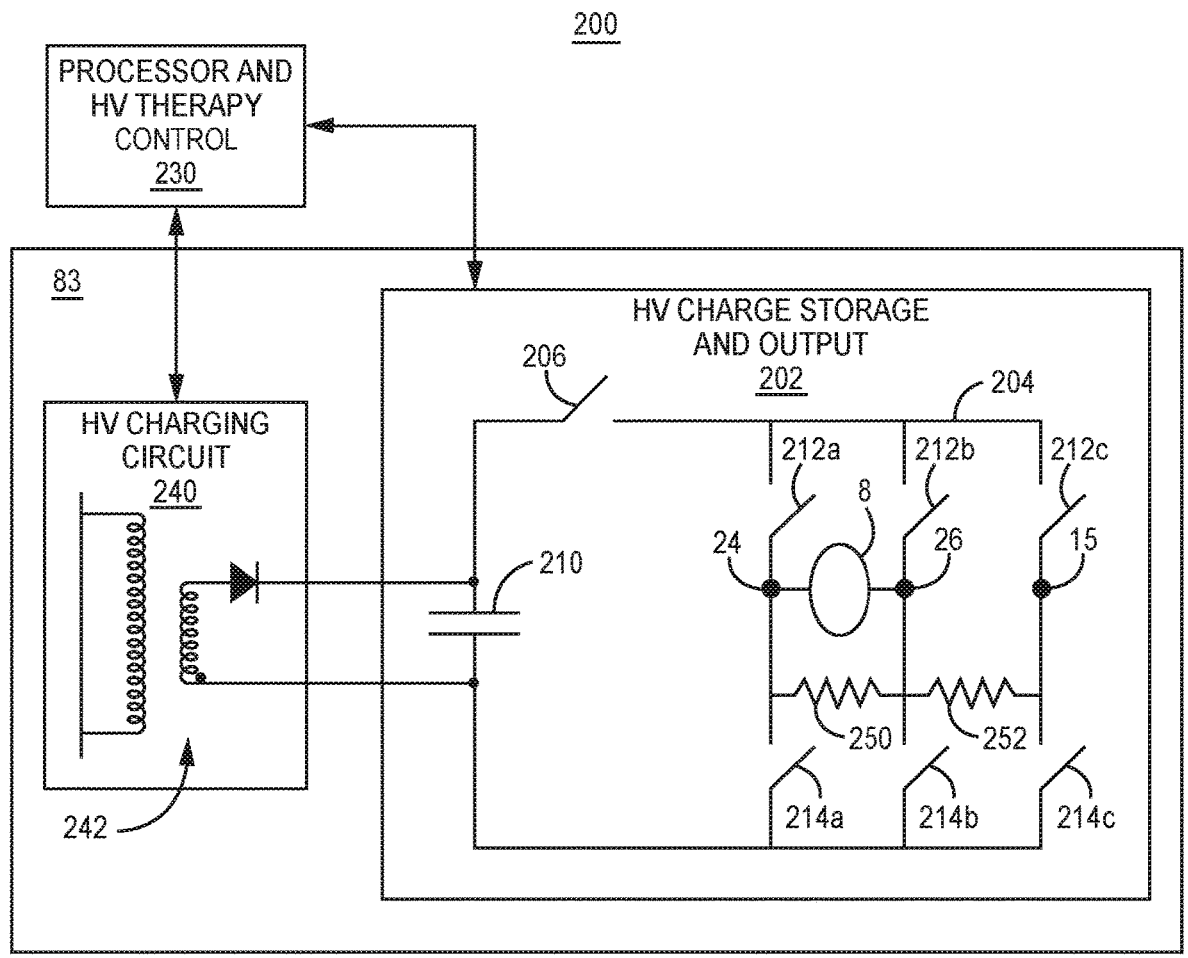
FIG. 4 is a schematic diagram of high voltage therapy circuit coupled to a processor and HV therapy control circuit.

FIG. 4 is a schematic diagram 200 of HV therapy circuit 83 coupled to a processor and HV therapy control circuit 230. HV therapy circuit 83 includes a HV charging circuit 240 and a HV charge storage and output circuit 202. Processor and HV therapy control circuit 230 may be included in control circuit 80 for controlling HV charging circuit 240 and HV charge storage and output circuit 202.

HV charge storage and output circuit 202 includes a HV capacitor 210 coupled to switching circuitry 204 via a pulse control switch 206 for electrically coupling the HV capacitor 210 to electrodes 24 and 26 and/or housing 15 to deliver a desired HV electrical stimulation pulse to the patient's heart 8. HV capacitor 210 is shown as a single capacitor, but it is recognized that a bank of two or more capacitors or other energy storage devices may be used to store energy for producing electrical signals delivered to heart 8. In one example, HV capacitor 210 is a series of three capacitors having an effective capacitance of 148 microfarads, 155 microfarads, or other selected capacitance. In contrast, holding capacitors that are included in LV therapy circuit 85 that are charged to a multiple of the battery voltage by a state machine may have a capacitance of up to 6 microfarads, up to 10 microfarads, up to 20 microfarads or other selected capacitance, but all have a capacitance significantly less than the effective capacitance of HV capacitor 210. The LV therapy circuit 85 has a lower breakdown voltage than the HV therapy circuit 83, allowing the HV capacitor 210 to be charged to the shock voltage amplitude, e.g., 100 V or more, required for delivering CV/DF shocks.

Switching circuitry 204 may be in the form of an H-bridge including switches 212a-212c and 214a-214c that are controlled by signals from processor and HV control circuit 230. Switches 212a-212c and 214a-214c may be implemented as silicon-controlled rectifiers (SCRs), insulated-gate bipolar transistors (IGBTs), metal-oxide-semiconductor field-effect transistors (MOSFETs), and/or other switching circuit components or combinations thereof.

When control circuit 80 determines that delivery of an electrical stimulation pulse from HV therapy circuit 83 is needed, switching circuitry 204 is controlled by signals from processor and HV therapy control circuit 230 to electrically couple HV capacitor 210 to a therapy delivery vector to discharge capacitor 210 across the vector selected from electrodes 24, 26 and/or housing 15. The selected electrodes 24, 26 and/or housing 15 are coupled to HV capacitor 210 by opening (i.e., turning off or disabling) and closing (i.e., turning on or enabling) the appropriate switches of switching circuitry 204 to pass a desired electrical signal to the therapy delivery electrode vector. While only electrodes 24, 26 and housing 15 are indicated as being coupled to switching circuitry 204, it is to be understood that pace/sense electrodes 28 and 30 may be coupled to switching circuitry 204 and available for use in a pacing electrode vector.

When control circuit 80 determines that a shock therapy is needed based on a detected heart rhythm, e.g., VT or VF, the electrical signal delivered by HV therapy circuit 83 may be a monophasic, biphasic or other shaped CV/DF shock pulse for terminating the ventricular tachyarrhythmia. When control circuit 80 determines that a pacing therapy is needed based on a detected heart rhythm or a pacing escape interval expiring, the electrical signals delivered by HV therapy circuit 83 include alternating polarity pulses with every nth pulse being modified to provide charge balancing. Modification of every nth pulse may include modification of the polarity, pulse amplitude, and/or pulse width compared to an expected, unmodified pattern of the alternating polarity pulses.

The pacing pulse may be terminated when the pulse voltage amplitude has decayed according to a programmed "tilt." Tilt is the percentage of the leading voltage amplitude that the pulse has decayed to. For example, the pacing pulse may be terminated at a tilt of 50%, when the pulse amplitude has decayed to 50% of the leading voltage amplitude. If the programmed tilt is 20%, the pacing pulse may be terminated when the pulse amplitude has decayed by 20%, i.e., to 80% of the leading voltage amplitude. In other examples, the pacing pulses delivered by HV pacing circuit 83 are terminated according to a predetermined pulse width.

Processor and HV therapy control circuit 230 controls charging of capacitor 210 to a programmed pacing pulse voltage amplitude or a modified, charge-balancing pacing pulse voltage amplitude. Switches 212a-212c and 214a-214c are controlled to be open or closed by processor and HV therapy control circuit 230 at the appropriate times for delivering a monophasic, biphasic or other desired pacing pulse by discharging capacitor 210 across the pacing load presented by heart 8 and a selected pacing electrode vector, e.g., electrodes 24 and 26. The capacitor 210 is coupled across the selected pacing electrode vector for a programmed or modified pacing pulse width or according to a programmed tilt.

Processor and HV therapy control 230 may control HV therapy circuit 83 to deliver cardiac pacing pulses by controlling HV therapy circuit 83 to deliver alternating polarity pacing pulses. Inherent limitations of the therapy delivery circuit 84 may result in charge imbalanced alternating polarity pacing pulses. For example, a net 10% charge difference may exist between a positive-going pulse and a negative going pulse that are controlled by therapy delivery circuit 84 according to the same programmed pulse amplitude (though opposite in polarity) and the same programmed pulse width (or tilt). Over time this small charge difference accumulates and may lead to electrode corrosion. In this example, assuming that each positive polarity pulse delivers approximately 10% greater charge than each negative polarity pulse, control circuit 80 may deliver ten alternating polarity pulses (+−+−+− . . . ) and modify the polarity of every eleventh pulse to be a negative polarity pulse (instead of the expected positive polarity) such that two consecutive negative polarity pulses are delivered, to balance the net positive charge accumulated over the preceding ten, alternating polarity pulses. In other examples, processor and HV therapy control 230 may control HV therapy circuit 83 to deliver every nth pacing pulse with a modified pulse amplitude and/or modified pulse width (compared to the programmed pacing pulse amplitude and pulse width of the preceding alternating polarity pulses) to balance charge accumulated in one or more preceding pacing pulses. The examples presented herein generally refer to the nth pulse of a series of n pulses being the modified, charge balancing pulse. It is contemplated, however, that the modified charge balancing pulse is not necessarily the last pulse of a series of n pulses. Any pulse in a series of n pulses may be the modified, charge balancing pulse that reduces or eliminates the net charge accumulated over the other n−1 pulses in the series of n pulses.

Before the first pulse, the HV capacitor 210 may be charged to the programmed pacing pulse voltage amplitude. HV capacitor 210 is recharged between consecutive pulses to the programmed pacing pulse voltage amplitude. HV charging circuit 240 is powered by power source 98 (FIG. 3). HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV therapy control 230, which receives feedback signals from HV charge storage and output circuit 202 to determine when capacitor 210 is charged to a programmed voltage. A charge completion signal is passed to HV charging circuit 240 to terminate charging by processor and HV therapy control circuit 230. One example of a high voltage charging circuit and its operation is generally disclosed in U.S. Pat. No. 8,195,291 (Norton, et al.), incorporated herein by reference in its entirety.

Switches 212a-212c and switches 214a-214c may require a minimum current flow to hold them closed (i.e., ON or enabled) for passing current as HV capacitor 210 is discharged. The minimum current to enable (close) switches 214a-214c may be approximately 10 milliamps or less than 10 milliamps depending on the pacing load impedance and other conditions. The electrical current passing through the enabled ones switches 212a-212c and 214a-214c may fall below the minimum current required to keep the enabled switches closed as capacitor 210 is discharged across a selected pacing electrode vector. If the current passing through a respective switch falls below the minimum current required to keep the switch closed, the switch may open (or become disabled) causing premature truncation of the pacing pulse, which could result in loss of capture and/or inadequate charge balancing. As such, a minimum pacing pulse voltage amplitude may be set for delivering pulses from HV therapy circuit 83 in order to reduce the likelihood of the electrical current falling below the minimum current required to maintain a stable state of enabled switches of switching circuitry 204 during a programmed pacing pulse width (or until a programmed tilt has been reached).

In other examples, HV charge storage and output circuit 202 may include an optional shunt resistance 250, 252 in parallel to the pacing load to maintain a minimum current through the switching circuitry 204. Shunt resistance 250 is shown in parallel to the pacing load shown schematically as heart 8 when electrodes 24 and 26 are selected as the anode and cathode (or cathode and anode, respectively) of the pacing electrode vector. It is recognized that a shunt resistance may be provided in parallel to the pacing load for any selected pacing electrode vector, for example shunt resistance 252 is shown schematically if the pacing electrode vector includes electrode 26 and housing 15. Likewise a shunt resistance may be provided in parallel to the pacing load when the pacing electrode vector includes electrode 24 and housing 15. The shunt resistance 250 or 252 may be a variable resistance that is set to match the pacing electrode vector impedance so that the load across heart 8 using a selected pacing electrode vector matches the shunt resistance. In this way, current through the switching circuitry 204 may be maintained at or above a minimum current required to maintain a stable state of enabled switches of switching circuitry 204 during the pacing pulse. Other examples of the use of a shunt resistance in switching circuitry 204 are generally disclosed in the above-incorporated U.S. patent application Ser. No. 15/425,169.

In some examples, the pacing electrode vector coupled to HV capacitor 210 via switching circuitry 204 may include electrodes 24, 26, 28 and/or 30 carried by lead 16. Housing 15 may be unused for cardiac pacing pulse delivery by holding switches 212c and 214c open. Depending on the implant location of ICD 14 and lead 16 and the resulting electrical stimulation delivery vector between the housing 15 and an electrode 24, 26, 28 and/or 30, greater recruitment of skeletal muscle may occur when housing 15 is included in the pacing electrode vector. A larger volume of skeletal muscle tissue may lie along a vector extending between the distal portion 25 of lead 16 and housing 15 than along a vector extending between the two electrodes carried by lead distal portion 25. In other electrode configurations and implant locations, however, the electrodes (which may include ICD housing 15) used to deliver extra-cardiovascular pacing pulses by HV therapy circuit 83 may be selected to provide a pacing electrode vector that minimizes the volume of skeletal muscle included in the pacing electrode vector while directing sufficient energy to the heart 8 for capturing and pacing the heart.

Figure 5:
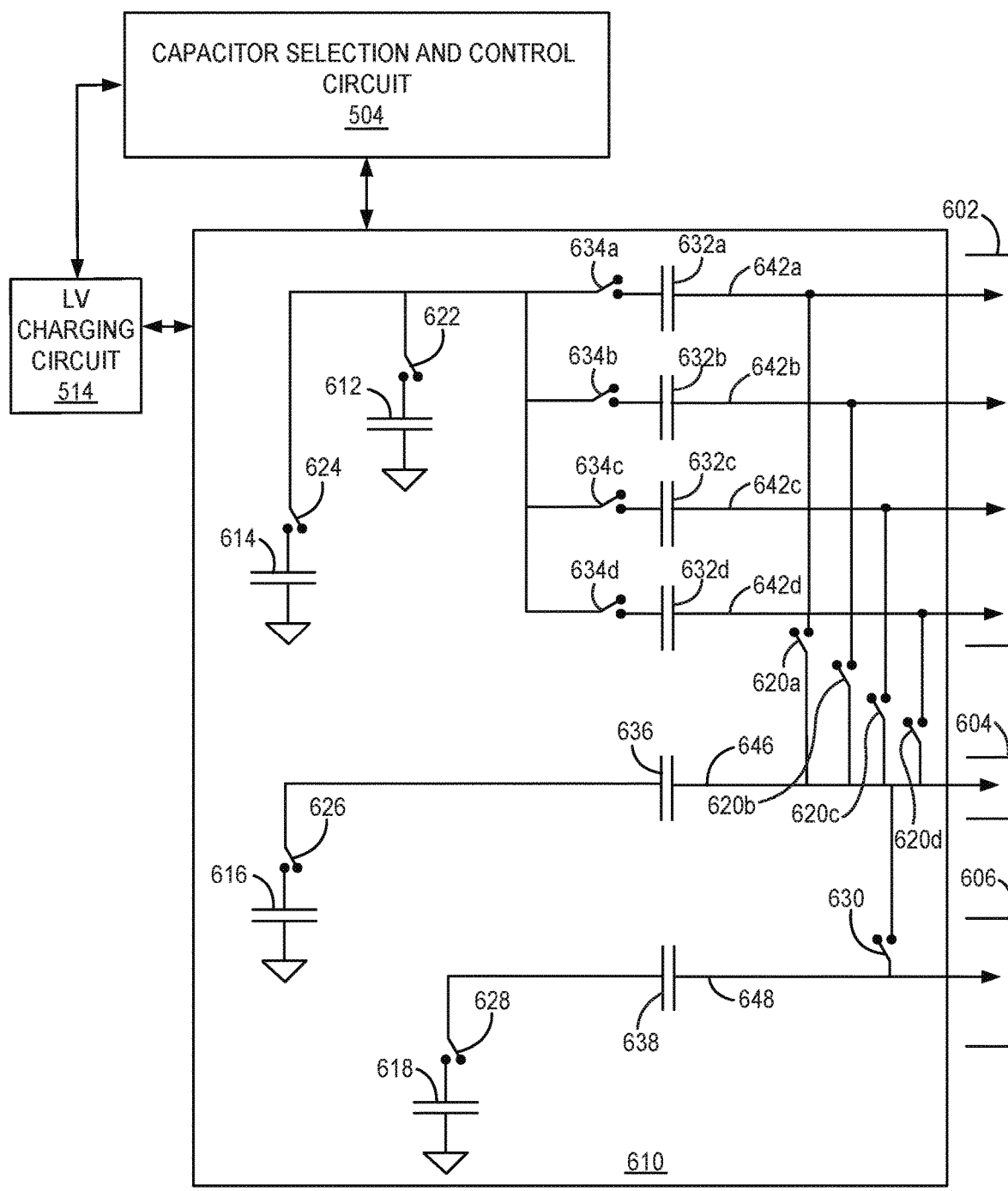
FIG. 5 is a conceptual diagram of a low voltage therapy circuit according to one example.

FIG. 5 is a conceptual diagram of LV therapy circuit 85 according to one example. LV therapy circuit 85 may include a capacitor selection and control circuit 504, a LV charging circuit 514, and a capacitor array 610. Capacitor array 610 may include multiple holding capacitors 612, 614, 616 and 618 that can each be charged by LV charging circuit 514 to a programmed pacing pulse amplitude. The holding capacitors 612, 614, 616 and 618 are coupled to a respective output capacitor 632a-632d (collectively 632), 636, or 638 via respective switches 622, 624, 626, and 628 to deliver pacing pulses. Each of holding capacitors 612, 614, 616 and 618 has a capacitance that is less than the effective capacitance of high voltage capacitor 210 of HV therapy circuit 83. For example each of holding capacitors 612, 614, 616 and 618 may have a capacitance of up to 6 microfarads, up to 10 microfarads, up to 20 microfarads or other selected capacitance, but all have a capacitance significantly less than the effective capacitance of high voltage capacitor 210.

Power source 98 (FIG. 3) may provide regulated power to LV charging circuit 514. LV charging circuit 514 may be controlled by a state machine in capacitor selection and control circuit 504 to charge all or selected ones of holding capacitors 612, 614, 616 and 618 using a multiple of the battery voltage of power source 98, e.g., four times the battery voltage. LV charging circuit 514 charges capacitors 612, 614, 616 and/or 618 as needed for delivering pacing pulses, which may be single pacing pulses (e.g., monophasic or biphasic) or composite pacing pulses during fused pacing. Composite pacing pulses include two or more individual pulses delivered successively so that the pulse energy of the successive individual pulses is effectively "fused" in time to deliver cumulative pacing pulse energy greater than the cardiac capture threshold. Fused pacing using composite pacing pulses delivered by a LV pacing circuit for extra-cardiovascular pacing is generally disclosed in U.S. Patent Application Publication No. 2017/0157399 (Anderson, et al.), incorporated herein by reference in its entirety.

In some examples, the LV therapy circuit 85 includes three pacing channels 602, 604 and 606. Each pacing channel is capable of producing a single pacing pulse when a respective holding capacitor 612, 616 or 618 is discharged across an output capacitor 632, 636, or 638, respectively. Pacing channel 602 includes a back-up holding capacitor 614 that may be used for delivering back-up pacing pulses, e.g., when a single pulse pacing output is selected. Back-up holding capacitor 614 may be used to deliver an individual pulse of a composite pacing pulse when fused pacing is being delivered.

Depending on the number of extra-cardiovascular electrodes coupled to ICD 14, one or more channels may include multiple selectable output signal lines. For example, channel 602 is shown in this example to include multiple selectable pacing output signal lines 642a-642d that may be selectively coupled to holding capacitor 612 and back-up holding capacitor 614 via closure of one or more of electrode selection switches 634a-634d. For example, multiple electrodes carried by lead 16 may be coupled to pacing channel 602 and a pacing electrode vector may be selected from the multiple electrodes by closing certain ones of switches 634a-634d.

Pacing channels 604 and 606 are shown having single output signal lines 646 and 648 that are coupled to respective holding capacitors 616 and 618 via respective switches 626 and 628. In other examples, all three pacing channels 602, 604 and 606 may be provided with a single output signal line or with multiple output signal lines to enable selection of a pacing electrode vector from among multiple extra-cardiovascular electrodes coupled to ICD 14, e.g., any of electrodes 24, 26, 28 or 30 of lead 16.

A single channel pacing output configuration may be enabled by control circuit 80 using any one of the pacing channels 602, 604 and 606 to deliver single-pulse pacing pulses. The single-pulse pacing may be delivered by discharging one of the holding capacitors 612, 614, 616 or 618 across a selected pacing electrode vector via a respective output capacitor 632, 636 or 638 when a respective switch 622, 624, 626 or 628 is closed. The output line 642a, 642b, 642c, or 642d used to deliver pacing current from pacing channel 602 may be selected via a respective electrode selection switch 634a-634d. The switches 622, 624, 626 or 628 that enable discharge of a holding capacitor 612, 614, 616, or 618, respectively, may be enabled by capacitor selection and control circuit 504 at the appropriate time when a pacing pulse is needed and maintained in an active, enabled state until the single pacing pulse width is expired.

When control circuit 80 is configured to deliver fused pacing using LV therapy circuit 85, the pacing channels 602, 604 and 606 are tied together by switches 620a-620d and 630 to enable individual pulses to be delivered across a selected pacing electrode vector from a single output signal line, e.g., line 646. For example, control circuit 80 may enable the fused pacing pulse output by activating switches 620a-620b and 630 to tie pacing output lines 642a-642d and pacing output line 648 to pacing channel 604. Control circuit 80 controls capacitor selection and control circuit 504 to enable pacing channel switches 622, 624, 626 and 628 (and at least one electrode selection switch 634a-634d of pacing channel 602) in a sequential manner to couple a respective holding capacitor 612, 614, 616 or 618 to output signal line 646 to deliver a sequence of fused, individual pulses to produce a composite pacing pulse.

In various examples, depending on the particular pacing channel and lead and electrode configuration used with ICD 14, some electrode selection switches shown in FIG. 5 may not be required. Furthermore it is recognized that less than four holding capacitors or more than four holding capacitors may be included in a capacitor array 610 for use in delivering a sequence of fused pacing pulses.

Capacitor selection and control circuit 504 selects which holding capacitors 612, 614, 616 and 618 are coupled to output line 646 and in what sequence by controlling respective switches 622, 624, 626 and 628. A sequence of pulses may be delivered to produce a composite pacing pulse by sequentially discharging holding capacitors 612, 614, 616 and 618 one at a time (or one combination at a time) across a respective output capacitor 632, 636 and 638 by sequentially enabling or closing the respective switches 622, 624, 626 and 628. For example, at least two of holding capacitors 612, 614, 616 and 618 are sequentially discharged to produce a composite pacing pulse produced by at least two fused individual pulses. Output line 646 may be electrically coupled to a pacing cathode electrode carried by lead 16 and a return anode electrode carried by lead 16 (or housing 15) may be coupled to ground. The pacing cathode electrode and return anode electrode may correspond to electrodes 24 and 28 or any pacing electrode vector selected from electrodes 24, 26, 28 and 30 and/or housing 15 shown in FIGS. 1A-2B.

In some examples, a fused pacing pulse is delivered by delivering two consecutive individual pulses from pacing channel 604 and 606 one at a time followed by a third, longer individual pulse delivered by pacing channel 602 by discharging both capacitors 612 and 614 simultaneously. The first two individual pulses may be 2.0 ms in pulse width and the third pulse may be 4.0 ms in pulse width for a composite pacing pulse width of 8 ms. The higher capacitance of the parallel capacitors 612 and 614 allows for the third individual pulse to be longer in pulse width while maintaining a pulse amplitude for the duration of the pulse width that successfully captures the heart. All three individual pulses are delivered via output line 646 because output configuration switches 620 and 630 are enabled for the fused pacing output configuration. In other examples, selected ones of holding capacitors 612, 614, 616, and 618 are discharged sequentially, individual or in combination, to deliver a series of pulses closely together in time to form a composite pacing pulse.

LV therapy circuit 85 may be controlled by control circuit 80 to deliver every nth pulse of a series of alternating polarity pacing pulses with a modified polarity, modified pulse amplitude, and/or modified pulse width to balance an unbalanced charge delivered over the preceding n-1 pacing pulses. The n-1 unmodified, alternating polarity pacing pulses may be delivered as alternating polarity single-pulse pacing pulses or as alternating polarity composite pacing pulses comprising two or more fused pulses. Modification of the nth pulse may include modifying the expected polarity of the nth pulse in the pattern of alternating polarity pulses by delivering two consecutive pulses (the nth-1 pulse and the nth pulse) having the same polarity, either both positive or both negative. Modification of the nth pulse may include modifying the expected pulse amplitude and/or pulse width by increasing or decreasing the pulse amplitude and/or pulse width from the programmed pacing pulse amplitude and/or programmed pacing pulse width, respectively, which is used to control the preceding n-1 pulses.

In the examples presented herein, the electrical stimulation pulses including opposing polarity pulses are voltage-controlled pulses such that the charge balancing nth pulse of a series of pulses may have a modified voltage amplitude. It is recognized however, depending on the medical device, the electrical simulation pulses may be current-controlled pulses and, as such, the modification to the charge balancing nth pulse may be a modified current amplitude.

Figure 6:
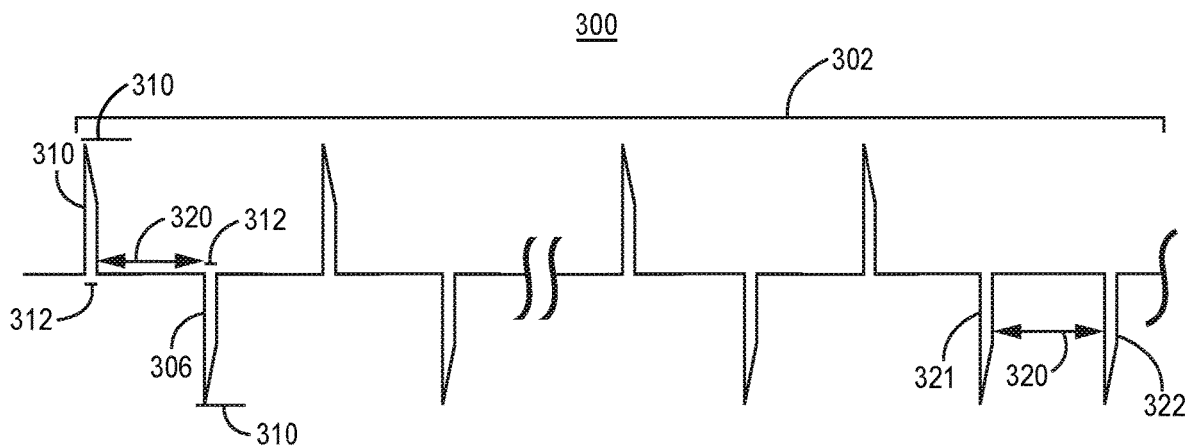
FIG. 6 is a conceptual diagram of a series of alternating-polarity pacing pulses including a charge balancing pulse.

FIG. 6 is a conceptual diagram 300 of a series of alternating polarity pacing pulses 302 including a charge balancing pulse 322. The series of n pulses 302 includes positive polarity pulses 304 and negative polarity pulses 306 that are delivered in alternation. The pulses are shown as monophasic pulses, but could be biphasic or other shaped pulses in other examples. The series of n pulses 302, including opposing polarity pulses, and series of pulses 350 and 380 shown in FIGS. 7 and 8, respectively, may represent a variety of electrical stimulation pulses that are delivered by a medical device to body tissue of a patient. In the illustrative examples described herein, the pulses may be cardiac pacing pulses which include opposing polarity pacing pulses and an nth charge balancing pacing pulse. In one example, control circuit 80 may control either HV therapy circuit 83 or LV therapy circuit 85 to deliver the alternating polarity pacing pulses 304 and 306 of the series of n pulses 302.

The alternating polarity pulses 304 and 306 may be separated in time by a pacing pulse interval 320. The pacing pulse interval 320 may be a lower rate interval used to pace the heart when the intrinsic rate falls below the programmed lower rate. The lower rate interval may be adaptively controlled according to a sensor-indicated patient activity to provide rate responsive pacing in some examples. The pacing pulse interval 320 may alternatively be an ATP interval, a post-shock pacing interval, or other pacing interval set by control circuit 80 according to a programmed cardiac pacing therapy protocol. Pacing pulse interval 320 may stay constant during the series of n alternating pacing pulses 302 or may vary, according to the pacing protocol. In some examples, the pacing pulse interval 320 may be controlled by the expiration of an escape interval counter included in control circuit 80.

In other examples, the pacing pulses 302 may represent ventricular pacing pulses being delivered in an atrial-tracking pacing mode or during CRT such that each pulse 304 and 306 is delivered upon the expiration of an AV pacing interval (not shown), in which case pulses 304 and 306 may be separated by variable intervals that depend on the atrial rate being tracked. In this case, the interval 320 between pulses does not necessarily represent a pacing escape interval. Furthermore, is to be understood that consecutive alternating polarity pacing pulses may occur with extended periods of time (e.g., one or more unexpired pacing escape intervals) with intervening intrinsic cardiac events occurring in some cases. As such, one positive pacing pulse consecutively occurring with one negative pacing pulse in a pair of alternating polarity pulses are not required to occur on consecutive cardiac cycles. None, one or more intrinsic cardiac cycles may occur between the positive and negative polarity pacing pulses of a charge imbalanced pair of alternating polarity cardiac pacing pulses.

Both of the positive polarity pulses 304 and the negative polarity pulses 306 may be delivered according to the same programmed pulse amplitude 310 and pulse width 312 (or tilt), which may be selected based on cardiac capture threshold testing. Inherent system limitations, however, may result in a net difference in the charge delivered during one pair of one positive pacing pulse 304 and one negative pacing pulse 306. Depending on the frequency of pacing, even a small charge imbalance of each pair of alternating polarity pulses may result in an accumulation of imbalanced charge over time. Every nth pacing pulse 322 of series 302 is modified by reversing the polarity of the nth pulse in the alternating pattern of pacing pulses. The modified nth pacing pulse 322 is delivered having a polarity that is the opposite polarity of the charge imbalance of a pair of one positive and one negative pulse to balance or offset accumulated charge. The charge delivered during each positive pacing pulse 304 may be a known or approximated percentage greater than the charge delivered during each negative polarity pulse 306 such that the pair of pulses has a net positive charge delivered or imbalanced positive charge. In other cases, the negative polarity pulse 306 may deliver a greater charge than the positive pulse 304 resulting in a net negative charge accumulation that is balanced by a positive polarity charge balancing pulse.

The value of n for controlling how often a modified, charge balancing pacing pulse is delivered may be based on the net charge difference between the positive and negative polarity pulses 304 and 306. For instance n may be determined as twice the reciprocal of the charge imbalance plus one or $n=2*(1/c)+1$ where c is the percentage charge imbalance (in decimal form) of one alternating pair of one positive and one negative polarity cardiac pacing pulse. Every nth pulse 322 may be modified by delivering it having the opposite polarity of the imbalanced charge. To illustrate, if the positive polarity pulses 304 are approximately 10% greater in charge delivery than the negative polarity pulses 306, a net positive charge equal to approximately 100% of the charge of one positive going pulse is accumulated after a series of 20 alternating pulses (10 positive-going pulses and 10 negative-going pulses). To balance the accumulated positive charge of 10% per alternating pacing pulse pair, control circuit 80 may determine that n=21 (21=2(1/0.1)+1). Every $21^{st}$ pulse of the alternating polarity pulses is therefore modified by delivering it with a negative polarity to balance the accumulated imbalanced positive charge of the preceding 20 pulses. In this way, any net charge that accumulates over the preceding n−1 alternating pulses is substantially balanced by the nth pulse.

The examples presented herein refer to a series of n−1 alternating polarity pulses followed by an nth pulse of the series being modified to provide charge balancing. It is contemplated, however, that the n−1 pulses may include any series of electrical stimulation pulses that results in a net charge accumulation that is offset by the nth pulse of the series. For instance, the n−1 pulses may include charge imbalanced, opposing polarity pulses but not necessarily in an alternating pattern of every other pulse being positive and every other pulse being negative. A series of pulses may include two, three or more consecutive positive polarity pulses followed by a like number of negative polarity pulses and that pattern may repeat until the nth modified, charge balancing pulse. To illustrate, the series of pulses including opposing polarity pulses may include two positive pulses followed by two negative pulses (+, +, −, −, +, +, −, −, +, + . . . ), and the series may be terminated with the modified charge balancing pulse.

While cardiac pacing pulses continuing after series 302 are not shown in FIG. 6, it is to be understood that series 302 may be n pacing pulses out of ongoing cardiac pacing pulses that are delivered according a programmed pacing therapy or pacing mode. For example, ICD 314 may be programmed to deliver cardiac pacing in VVI, VDI, or VDD pacing mode (with or without rate response) such that pacing may be occurring over an extended period time and series 302 represents n pacing pulses delivered during the ongoing pacing. During the ongoing pacing, every nth pulse may be modified by delivering it at the same polarity as the pulse polarity having an inherently lesser net charge. As a result, every n−1 and nth pulses during ongoing pacing may have the same polarity to balance a net charge accumulated over the n−1 pulses. Polarity alternation may resume with the next n+1 pulse being the opposite polarity of the nth pulse, and being the first pulse of the next series of n pulses ending with a modified nth pulse. For example, if every 5th pulse is modified to balance a net charge delivered during the preceding four alternating polarity pulses, the pacing pulse polarity may be represented by: +−+−−+−+−−+−+−−+ . . . and so on. In other examples, the series of pacing pulses 302 may represent all pulses delivered during an ATP or other pacing therapy in which the last pacing pulse may be the nth pulse 322 that is modified to balance the charge delivered over the preceding n−1 pulses of the pacing sequence.

Figure 7:
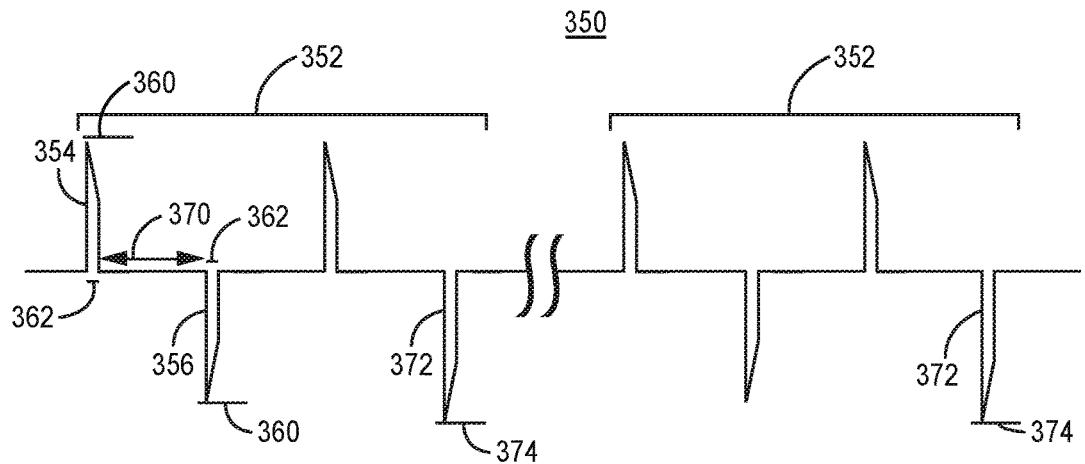
FIG. 7 is a diagram of cardiac pacing pulses delivered according to another example technique for charge balancing.

FIG. 7 is a diagram 350 of cardiac pacing pulses delivered according to another example technique for charge balancing. In this example every nth pulse 372 of each series of n pulses 352 is modified by adjusting the pacing pulse amplitude 374 of the nth pulse 352. Each unmodified positive polarity pulse 354 and each unmodified negative going pulse 356 is delivered by therapy circuit 84 according to a programmed pacing pulse amplitude 360 and pulse width 362 (or tilt). Despite being delivered according to the programmed pacing pulse amplitude 360 and pulse width 362, the alternating positive and negative pulses 354 and 356, respectfully, may deliver an inherently different charge resulting in an imbalanced charge delivery after each pair of one positive pulse 354 and one negative pulse 356. In the example shown, the nth pulse 372 of each series of n pulses 352 is modified by increasing the pulse amplitude 374 by a predetermined amount to balance a net positive charge accumulated during the preceding n−1 pulses. The increased pulse amplitude 374 is based on the inherently higher charge delivered with each positive polarity pulse 354 in this example.

For instance, if each positive pulse 354 delivers a 10% higher charge than each negative pulse 356, the modified negative polarity pulse 372 may have a modified pulse amplitude 374 that is adjusted to be greater than the unmodified pulse amplitude 360 to balance the 20% net positive charge imbalance of the preceding two pairs of one positive and one negative pulse. The value of the increased amplitude 374 may be determined based on bench testing or modeling of the charge imbalance between positive and negative pulses 354 and 356. The amplitude adjustment made to the modified pulse amplitude may be dependent on the lead and electrode vector impedance and other electrical stimulation pulse output factors. In the example shown, n=4 so that every fourth pulse is delivered at an increased pulse amplitude. In other examples, every other pulse (e.g., every positive pulse or every negative pulse) may be delivered with a modified pulse amplitude so that the series of pacing pulses 352 include alternating polarity and alternating pulse amplitude pulses. In this case each pair of one positive polarity pulse 354 and one negative polarity pulse 356 is delivered as a series of n=2 pulses and in a way that minimizes any inherent charge imbalance.

In some examples, control circuit 80 may be configured to establish how often a modified pulse is delivered and how much the pulse amplitude is adjusted in order to balance the preceding n−1 pulses based on the inherent charge difference between the positive and negative polarity pulses 354 and 356 and a maximum acceptable pulse amplitude of the modified, charge balancing pulse. If the charge imbalance of one pair of alternating polarity pulses is relatively high, n may be selected to have a relatively low value such that the modified nth pulse occurs relatively frequently with a reasonable and acceptable increase in pulse amplitude. If the charge imbalance of one pair of alternating polarity pulses is relatively low, a larger value of n may be selected so that the frequency of the modified, charge balancing pulse can be relatively lower, still with an acceptable higher pulse amplitude. An unacceptably high pulse amplitude may cause unintended capture of skeletal muscle or nerves in the vicinity of the pacing electrodes and cause patient discomfort.

While the modified pulse 372 is shown in FIG. 7 to have an increased pulse amplitude compared to the unmodified alternating polarity pulses 354 and 352 to offset a charge imbalance of the opposite polarity of the modified pulse 372, it is conceivable that a modified pulse in the series of n pulses could have a decreased pulse amplitude instead of an increased pulse amplitude. The decrease in amplitude may offset the inherently higher charge of the preceding pulses of the same polarity as the modified charge balancing pulse. The decreased pulse amplitude, however, may result in a loss of cardiac capture on the nth pulse, which may or may not be acceptable depending on the particular pacing application.

Figure 8:
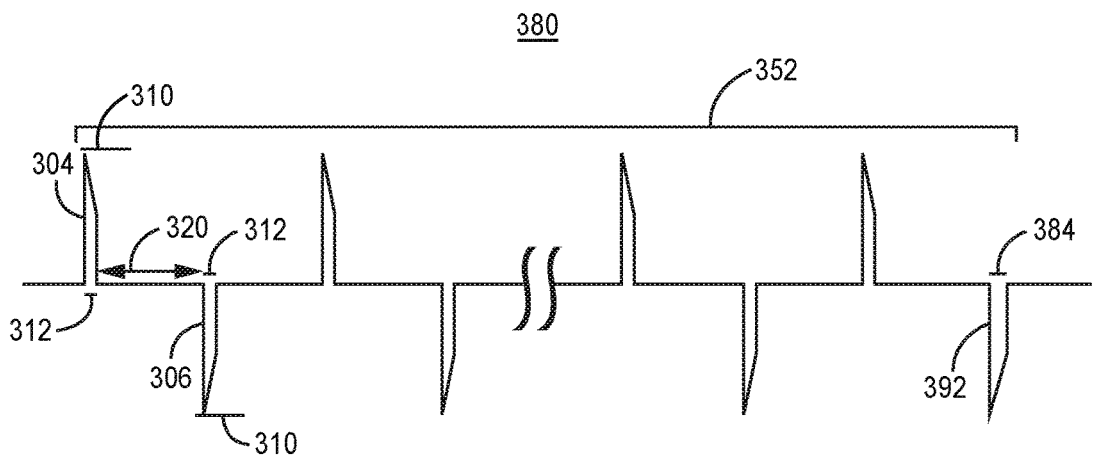
FIG. 8 is a diagram of another technique for delivering charge balancing cardiac pacing pulses.

FIG. 8 is a diagram 380 of another technique for delivering charge balancing cardiac pacing pulses. In FIG. 8, the nth pulse 392 of each series 382 of alternating cardiac pacing pulses 304 and 306 is modified by adjusting the pulse width 384 from the unmodified pulse width 312. The pulse width 384 may be increased or decreased to balance an accumulated net charge delivered over the preceding n−1 pulses. It is recognized that a decreased pulse width may result in a pacing loss of capture, which may or may not be acceptable. In the example shown, the nth pulse 392 is modified by increasing the pulse width 384 from the pulse width 312 of the unmodified pulses 304 and 306 to offset or balance a net positive charge accumulated during the delivery of the preceding n−1 pulses. The modified pacing pulse width may be determined based on a known inherent charge imbalance of each pair of unmodified, alternating polarity pacing pulses and the selected value of n. A selected value of n may have an upper limit based on a maximum pacing pulse width that is achievable by the RC time constant of the pacing circuit and acceptable in terms of overall delivered pacing pulse energy to the patient's heart. As such, if a relatively high charge imbalance exists, a lower value of n may be selected so that every nth pacing pulse is delivered with an acceptable and achievable increased pulse width 384 of the modified, charge balancing pulse 392.

In the above examples, the positive polarity pulse is described as inherently delivering a greater charge than the negative polarity pulse such that after each pair of one positive and one negative pacing pulse, a net positive charge is delivered. The modified nth pulse in these examples is described as being a negative polarity pulse. It is recognized, however, that the modified, nth pulse may be a positive polarity pulse that is adjusted to balance a charge imbalance. The charge imbalance may be due to a net positive polarity charge or due to a net negative polarity charge since, in some cases, the negative polarity pulses may inherently deliver a greater charge than the positive polarity pulses.

Each of the pulses shown in FIGS. 6-8 are cardiac pacing pulses that are intended to be therapeutic and therefore delivered at a pulse amplitude and width that is expected to cause cardiac capture and depolarization of the myocardial tissue. As such, each nth, charge balancing pacing pulse is also a therapeutic cardiac pacing pulse. In other examples, however, a modified nth pulse may be delivered during a physiological refractory period of the myocardium following the n−1 pulse such that the nth pulse is a non-therapeutic pulse that is delivered as a charge balancing pulse without the intention of causing cardiac capture. In other examples, the modification to the nth pulse may change the delivered pacing pulse energy to a level that is less than the pacing capture threshold. In this case, a loss of capture may occur, but loss of capture on one out of every n pacing pulses may be acceptable in some applications.

Figure 9:
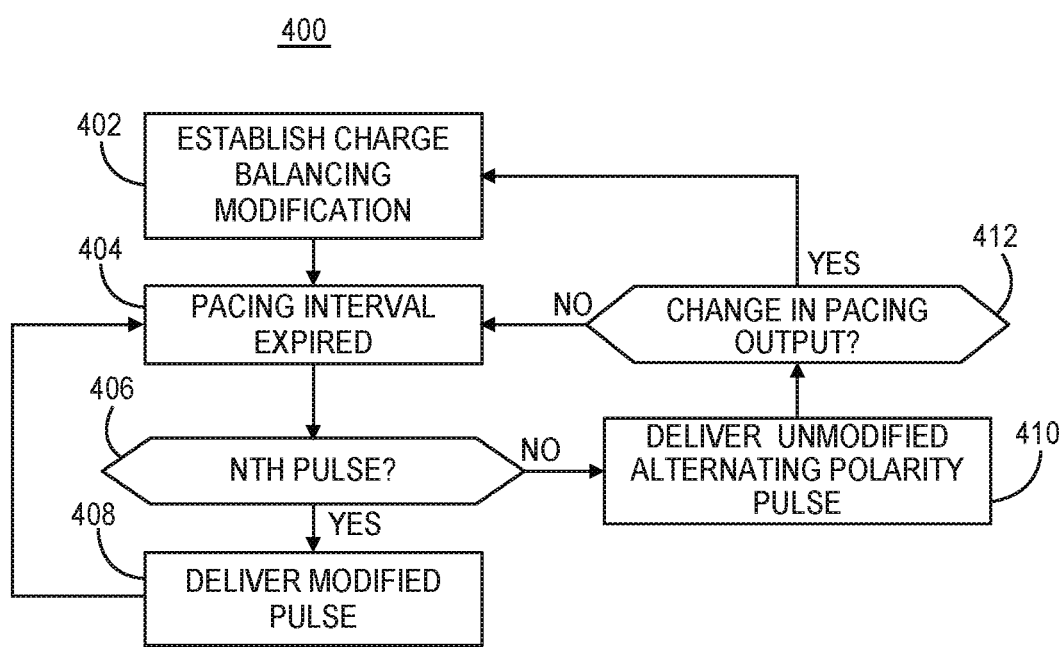
FIG. 9 is a flow chart of a method for delivering charge balancing cardiac pacing pulses according to one example.

FIG. 9 is a flow chart 400 of a method for delivering charge balancing cardiac pacing pulses according to one example. At block 402, control circuit 80 establishes one or more charge balancing pacing pulse modifications to be performed during cardiac pacing Control circuit 80 may control HV therapy circuit 83 or LV therapy circuit 85 to deliver extra-cardiovascular pacing pulses. Extra-cardiovascular pacing pulses generated by either the HV therapy circuit 83 or the LV therapy circuit 85 are relatively higher energy pacing pulses than pulses delivered by endocardial or epicardial electrodes. As such, control circuit 80 may establish a charge balancing pulse modification to be applied for use when HV therapy circuit 83 is being used to generate and deliver cardiac pacing pulses and the same or a different modification used when LV therapy circuit 85 is selected for generating and delivering cardiac pacing pulses. The charge balancing pacing pulse modification may be different when LV therapy circuit 85 is being used to generate and deliver cardiac pacing pulses than when HV therapy circuit 83 is being used since a different inherent charge imbalance may exist between the positive and negative polarity pulses generated by the two different circuits.

In some examples, charge balancing pacing pulse modifications may be stored in a lookup table (LUT) in memory 82 for one or more pacing output conditions. A known inherent charge difference between positive and negative polarity pulses generated by therapy circuit 84 may be determined at the time of manufacture of the ICD 14, e.g., through empirical or bench testing. The inherent charge difference may be determined for one or more pacing output conditions. For example, a different charge imbalance may exist between positive and negative polarity pulses generated by HV therapy circuit 83 than the charge imbalance between positive and negative polarity pulses generated by LV therapy circuit 85. Other pacing output conditions that may change the inherent charge difference between positive and negative polarity pulses may include the pacing electrode vector used to deliver the pulses, pacing electrode vector impedance, pacing pulse amplitude, pacing pulse width, and pacing rate, as examples and without limitation. An inherent charge difference and/or associated pacing pulse modification may be stored in memory 82 for each one of multiple pacing output conditions. The inherent charge difference(s) and/or corresponding pacing pulse modification(s) may be stored in one or more LUTs.

Control circuit 80 may therefore establish the charge balancing modification at block 402 by retrieving the modification from a LUT stored in memory 82 for a given pacing output condition or combination of conditions. For instance, one LUT may be stored in memory 82 for use when HV therapy circuit 83 is used for delivering cardiac pacing pulses. The LUT may include multiple ranges of pacing electrode vector impedance paired with multiple ranges of pacing pulse amplitude. Each cell in the LUT may store the modification to be applied for a given combination of impedance and pacing pulse amplitude when the HV therapy circuit 83 is selected for generating and delivering the pacing pulses. Another LUT may be stored in memory 82 for use when the LV therapy circuit 85 is selected for delivering cardiac pacing pulses. This LV therapy circuit LUT may include the same or a different combination of pacing output conditions than the HV therapy circuit LUT since different conditions may have a greater or lesser impact on the inherent charge imbalance produced by the two different therapy circuits 83 and 85. The LV therapy circuit LUT may include multiple ranges of pacing electrode vector impedance paired with multiple ranges of pacing pulse width, as an example.

Each cell in a charge balancing modification LUT may at least define the value of n, where n is the number of the modified pulse in a series of consecutive, alternating-polarity cardiac pacing pulses. Each cell in the LUT may also include one or more pacing pulse modifications to be applied to the nth pacing pulse. As described above in conjunction with FIGS. 6-8, the modifications may include polarity reversal, pulse amplitude adjustment, pulse width adjustment or any combination thereof.

In other examples, a LUT stored in memory 82 may store the inherent charge imbalance of a pair of alternating polarity pacing pulses for a given pacing output condition or combination of pacing output conditions. Control circuit 80 may be configured to determine the charge balancing modification at block 402 based on an inherent charge imbalance stored in memory 82. For example, one or more LUTs may be stored in memory 82 that list the inherent charge imbalance for the HV therapy circuit 83 for one or more output conditions such as pacing electrode vector, pacing impedance, pacing rate, pacing pulse amplitude and/or pacing pulse width. Likewise, one or more LUTs may store the inherent charge imbalance for the LV therapy circuit 83 for one or more output conditions. Control circuit 80 may retrieve the charge imbalance for a given pacing output configuration or condition and determine the pacing modification to be applied to every nth cardiac pacing pulse. In some cases, control circuit 80 only determines the value of n to control how often a charge balancing pacing pulse is delivered having a predetermined modification. The predetermined modification may be a reversal of polarity, a fixed pulse amplitude change and/or a fixed pulse width change.

When the charge balancing pulse is modified by switching its polarity, as described in conjunction with FIG. 6, establishing how often the modified pulse polarity is applied, e.g., every n pulses, may be the only parameter that control circuit 80 needs to determine at block 402 to establish the charge balancing modification based on a stored inherent charge imbalance. For example, control circuit may determine a value of n based on the imbalanced charge of each pair of one positive polarity pulse and one negative polarity pulse as described in conjunction with FIG. 6.

In examples that include adjusting the pulse amplitude and/or pulse width of the modified pulse, establishing the charge balancing modification at block 402 may additionally or alternatively include determining a pulse amplitude and/or pulse width adjustment applied to every nth pulse based on a stored, inherent charge imbalance. In some examples, n may be fixed such that using a known charge imbalance between positive and negative polarity pulses, control circuit may calculate an appropriate polarity, amplitude and/or pulse width adjustment that should be applied to the nth pulse to balance charge accumulated during the preceding n−1 pulses. Other examples of methods for establishing the charge balancing modification are described below in conjunction with FIG. 11.

Control circuit 80 may control the timing of pacing pulses delivered by therapy delivery circuit 84 by setting pacing escape interval timers or counters in accordance with a pacing mode or therapy. The pacing escape intervals may be programmed values stored in memory 82 (e.g., a fixed lower rate interval or an atrioventricular pacing interval), or automatically adjusted pacing intervals (e.g., a rate responsive temporary lower rate interval). Upon expiration of a pacing interval at block 404, control circuit 80 determines if the scheduled pacing pulse is the nth pulse of a series of consecutive alternating pacing pulses at block 406. For example, control circuit 80 may include a counter that counts each delivered pacing pulse up to (or down from) n−1 delivered pacing pulses so that the nth pulse is delivered as the modified, charge balancing pulse at block 408. If the scheduled pacing pulse is not the nth pulse, as determined at block 406, control circuit 80 controls therapy delivery circuit to deliver an unmodified cardiac pacing pulse at block 410 according to the programmed pacing pulse amplitude, width and alternating polarity.

Once the charge balancing modification is established at block 402, no adjustments to the modification may be required in some examples. In other examples, control circuit 80 may determine that a change in pacing output has occurred at block 412. One example of a change in pacing output is a change in pacing electrode vector impedance. Control circuit 80 may control impedance measurement circuit 90 to periodically monitor pacing electrode vector impedance (and/or in response to detecting loss of capture or selecting a new pacing electrode vector). If a change in impedance of the pacing electrode vector is detected (which may be due to a change in the selected pacing electrode vector), the charge imbalance between positive and negative polarity pulses may change. Other changes in pacing output detected at block 412 may include a change in the selection of the HV therapy circuit 83 or the LV therapy circuit 85 for generating the pacing pulses, a different pacing electrode vector selected for delivering pacing pulses, an adjustment of the pacing pulse amplitude, an adjustment of the pacing pulse width, and/or adjustment of a pacing mode (e.g., resulting in increased or decreased pacing rate or frequency).

Control circuit 80 may be configured to detect or identify a change in a pacing output condition that is associated with a change in the charge imbalance between positive and negative polarity pulses, warranting a change in the charge balancing modification established at block 402. In response to detecting a change in a pacing output condition that is associated with a change in charge imbalance, control circuit 80 may return to block 402 to select or determine a different charge balancing modification to account for a change in the charge imbalance of each pair of one positive and one negative polarity pacing pulse. Control circuit 80 may re-establish the charge balancing modification by retrieving data from LUTs stored in memory 82 as described above. If a change in pacing output is not detected at block 412, control circuit 80 continues to count alternating polarity pacing pulses (blocks 404 and 406) and controlling therapy delivery circuit 84 to deliver each nth pulse according to the established charge balancing modification at block 408.

Figure 10:
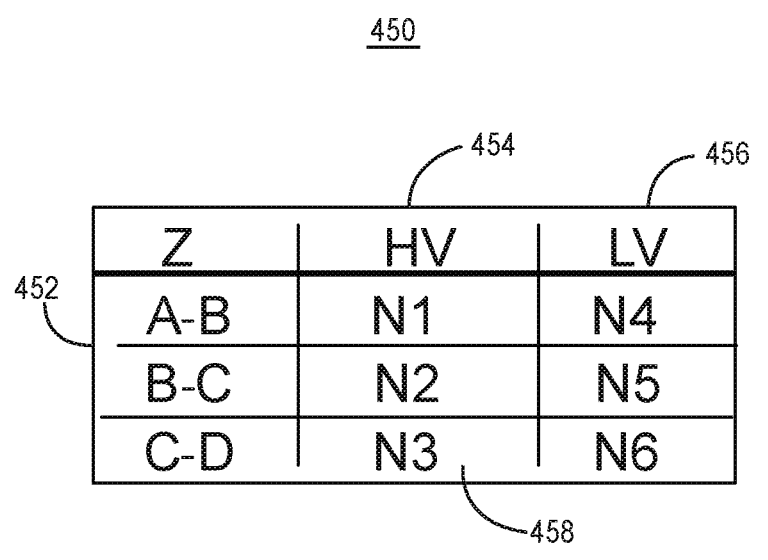

FIG. 10 is a conceptual diagram of one example of a LUT 450 that may be stored in memory 82 for control circuit 80 to retrieve charge balancing pacing pulse modifications from. In this example, a pacing output condition is shown in the first column 452 as the pacing electrode vector impedance Z. Three ranges of impedance are shown in the first column 452, but any desired number of pacing electrode vector impedances may be included in LUT 450. Other examples of a pacing output condition that may be listed in the rows of the first column 452 may include but are not limited to ranges of the unmodified pacing pulse amplitude, ranges of the unmodified pacing pulse width, or ranges of the pacing rate.

A different pacing condition is shown across the first row of LUT 450. In this example, a HV therapy circuit output configuration 454 and a LV therapy circuit output configuration 456 may be included in LUT 450. In other examples, separate LUTs may be provided for each of the HV therapy circuit and the LV therapy circuit and may be one-dimensional or multi-dimensional tables which store a parameter used by control circuit 80 for establishing a charge balancing modification for a given set of pacing output conditions. In the example shown, control circuit 80 may be configured to determine the pacing electrode vector impedance (using impedance measurement circuit 90) and the selected HV or LV therapy circuit for delivering pacing pulses and retrieve from a corresponding cell 458 the number n of the charge balancing modified pacing pulse. The nth pulse may be modified by reversing its polarity in the pattern of alternating polarity pulses.

In other examples, each cell 458 of LUT 450 may indicate a pulse amplitude and/or pulse width modification to apply to every nth pacing pulse, where n is a fixed, predetermined value. In still other examples, each cell 458 may include a value of n, a pulse amplitude adjustment, a pulse width adjustment and an indication of whether the polarity should be reversed from the normal alternating order or any combination thereof. The stored pulse amplitude adjustment may range from 0 up to a maximum amplitude adjustment, e.g., up to a 1 to 5 V increase from the unmodified pacing pulse amplitude. The stored pulse width adjustment may range from 0 up to a maximum pulse width adjustment, e.g., up to a 5 to 10 ms increase from the unmodified pacing pulse width. One or more LUTs may be stored in memory 82 for enabling control circuit 80 to retrieve charge balancing pacing pulse modifications to be applied for a determined combination of pacing output conditions.

In other examples, the LUT 450 may store in each cell 458 the net charge imbalance of one pair of one positive polarity pacing pulse and one negative polarity pacing pulse for a given combination of impedance and the selected therapy circuit, either HV therapy circuit 83 or LV therapy circuit 85. Control circuit 80 may perform a computation or algorithm for determining the charge balancing modification based on the retrieved net charge imbalance. For example, control circuit 80 may determine the value of n based on the net charge imbalance as described in conjunction with FIG. 6. Other mathematical functions modeling the relationship between pacing output conditions may be implemented in a processor of control circuit 80 for determining the charge balancing modification required to balance the retrieved net charge imbalance within predefined limits of pacing pulse amplitude and pacing pulse width.

Figure 11:
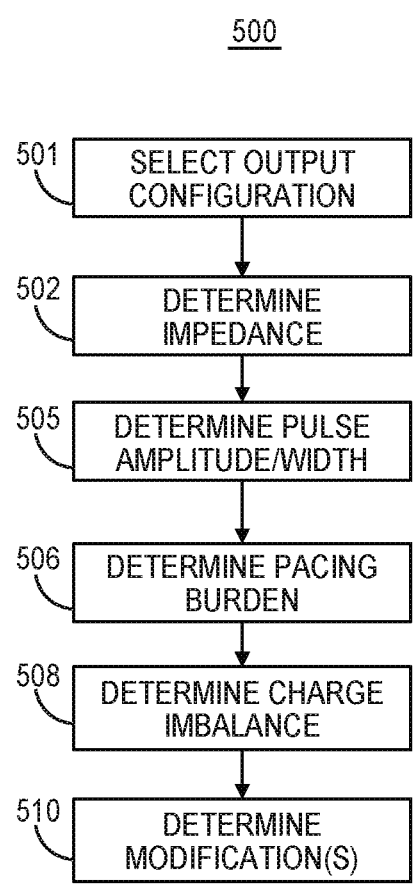
FIG. 11 is a flow chart of a method for establishing a modification of a charge balancing pacing pulse by an ICD according to one example.

FIG. 11 is a flow chart 500 of a method for establishing a modification of a charge balancing pacing pulse by control circuit 80 of ICD 314 according to one example. The process of flow chart 500 may be performed at block 402 of FIG. 9 or may be performed for generating a LUT, such as LUT 450 of FIG. 10. Control circuit 80 may be configured to perform an algorithm for determining a value of n (where n is the number of the modified pacing pulse in a series of consecutive pacing pulses), the polarity, the pulse amplitude and/or the pulse width of every modified nth pacing pulse. In order to determine the modification(s) of the charge balancing pacing pulse, control circuit 80 may determine one or more pacing output conditions that may change the inherent charge imbalance between a pair of one positive and one negative polarity pacing pulses.

Control circuit 80 may select the pacing output configuration at block 501. The pacing output configuration may be selected by selecting a therapy delivery output circuit and/or the pacing electrode vector. For instance, control circuit 80 may select the HV therapy circuit 83 or the LV therapy circuit 85 for delivering the pacing pulses via a selected pacing electrode vector. The LV therapy circuit 85 may be selected to deliver single-pulse pacing pulses or composite pacing pulses comprising multiple fused pulses delivered rapidly together.

Control circuit 80 may determine the impedance of the selected pacing electrode vector at block 502 by controlling impedance measuring circuit 90. Impedance may be determined by delivering a drive current signal across a selected pacing electrode vector and determining a resulting voltage developed across the electrode vector. At block 505, control circuit 80 may determine the pacing pulse amplitude and/or pacing pulse width of the cardiac pacing pulses. This determination may be made by performing a cardiac pacing threshold test for establishing the pacing pulse amplitude (or width) at a safety margin above the threshold pulse amplitude (or width). In other examples, the pacing pulse amplitude and width may be retrieved from memory 82 as stored pacing control parameters. While the determinations of pacing output configuration, electrode vector impedance and pulse amplitude and pulse width are shown as separate sequential steps in FIG. 11, it is to be understood that these determinations may be performed in a semi-simultaneous or integrated manner since the pacing output configuration selected at block 501 may depend on the determined pacing electrode vector impedance and the pacing pulse amplitude and pacing pulse width will depend on the capture threshold determined for a given pacing electrode vector.

At block 506, control circuit 80 may determine an expected or historical pacing burden or rate. The expected pacing rate may be based on a programmed lower rate and/or pacing mode. For example, an expected average pacing rate during a rate responsive VVIR pacing mode may be higher than the expected average pacing rate during a non-rate responsive VVI pacing mode with a low programmed lower rate such as 40 pulses per minute or during VDD pacing with minimized ventricular pacing.

At block 510, control circuit 80 may determine an expected accumulated charge imbalance after each pair of one positive and one negative polarity pacing pulse based on the impedance, pacing pulse amplitude and width, expected pacing rate, and output configuration. In some examples, control circuit 80 may utilize the relationship $Q=V*PW/Z$ for determining Q as the delivered charge of a pacing pulse having a pulse amplitude V (in volts) and pulse width PW in seconds, using a pacing electrode vector having an impedance Z. In another example, control circuit 80 may measure the current I (in Amperes) delivered during a pacing pulse having pulse width PW (in seconds) and utilize the relationship Q=I*PW for determining the charge Q delivered during the pacing pulse. The charge delivered for a set of pacing output conditions may be determined for a positive polarity pulse and for a negative polarity pulse for determining a net charge imbalance of the pair of one positive and one negative polarity pulse.

One or more pacing condition inputs may be used to model or estimate the resulting charge imbalance during empirical testing. For instance a mathematical model of the net charge imbalance for one or more independent pacing output conditions may be generated during bench testing of ICD 314. Control circuit 80 may provide the input pacing conditions to the model (stored in memory 82) to determine the predicted charge imbalance of each pair of alternating polarity pulses. The predicted net charge imbalance of one pair of opposite polarity pulses may be output from the mathematical model after inputting the conditions determined at blocks 501 through 506. Based on the predicted net charge imbalance of each pair of opposite polarity pacing pulses, control circuit 80 may determine the charge balancing modification to apply on every nth pacing pulse, which may include reversing the polarity, adjusting pulse amplitude and/or adjusting pulse width. Additionally or alternatively, control circuit 80 may be configured to determine n, the number of pacing pulses delivered in the series of alternating polarity pacing pulses ending with the modified charge balancing pulse and may apply a default modification, such as polarity reversal, to the nth pacing pulse. For example, if a net charge imbalance of 5% is determined based on the pacing output configuration and conditions determined at blocks 502 through 508, control circuit 80 may determine n to be 41. The $41^{st}$ pulse may be delivered with the opposite polarity of the charge imbalance of one pair of alternating polarity pulses to balance charge accumulated during the preceding 40 pacing pulses. Other examples of pacing pulse modification that control circuit 80 may determine at block 510 have been described above.

While the examples described above include modifying every nth pulse using the same modification(s) of polarity reversal, pulse amplitude and/or pulse width, it is further contemplated that the charge balancing cardiac pacing techniques disclosed herein may include modifying more than one pulse in a series of pulses, e.g., modifying every nth pulse using a first modification and modifying every mth pulse using a second modification different than the first modification. For instance, every nth pulse may be delivered with a modified pulse amplitude and every mth pulse may be delivered with a reversed polarity from the expected alternating polarity pattern. In one illustrative example, every $21^{st}$ pulse is modified according to a first modification and every $201^{st}$ pulse is modified according to a second modification. As such, in some examples, control circuit 80 may establish more than one charge balancing modification at block 510. A first modification of every nth pulse and a second modification of every mth pulse may be determined.

The modification of every mth pulse may minimize any residual charge imbalance that remains after delivering a preceding number of series of n pulses. For instance, if positive pulses deliver a 10% higher charge than negative pulses, the modified nth pacing pulse may be the $21^{st}$ pacing pulse delivered at negative polarity. This nth pulse may not balance 100% of the positive charge accumulated over the preceding 20 pulses, however. For example, the one negative pulse may balance 90% of the positive charge accumulated over the 20 preceding pulses since it delivers 10% less charge than the positive-going pulses. Therefore, every $201^{st}$ pulse may be delivered having a negative polarity to minimize residual charge after every twenty, modified nth pulses.

In such examples, m may have a higher value than the value of n. In other examples, m and n may be equal but are staggered such that in a series of pacing pulses the mth and nth pulses are spaced apart and may have different charge balancing modifications. For instance, if m and n are both equal to 5, in a series of 5 pulses the first two pulses may be unmodified (u), the third pulse may be modified according to the first modification (n), the fourth pulse may be unmodified and the fifth pulse may be modified according to the second modification (m) and this pattern of five pulses may repeat (u u n u m u u n u m . . . ). The second modification of every mth pulse may further reduce any charge imbalance that is not eliminated by the first modification of every nth pulse.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single device, circuit or unit for purposes of clarity, it should be understood that the techniques of this disclosure may be performed by a combination of units or circuits associated with, for example, one or more medical devices.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:
1. A medical device comprising:
a therapy delivery circuit comprising a pulse generator configured to generate and deliver electrical stimulation pulses via electrodes coupleable to the therapy delivery circuit; and a control circuit coupled to the therapy delivery circuit and configured to control the therapy delivery circuit to:

deliver a plurality of electrical stimulation pulses comprising at least one first pulse having a first polarity and at least one second pulse having a second polarity opposing the first polarity, the at least one first pulse and the at least one second pulse of the plurality of electrical stimulation pulses being charge imbalanced pulses delivering a net electrical charge; and deliver a charge balancing pulse by modifying every nth pulse of the plurality of electrical stimulation pulses to reduce the net electrical charge delivered over the plurality of electrical stimulation pulses.

2. The device of claim 1, wherein the control circuit is configured to control the therapy delivery circuit to deliver the plurality of electrical stimulation pulses as alternating polarity pulses.

3. The device of claim 1, wherein the control circuit is configured to:

control the therapy delivery circuit to deliver the plurality of electrical stimulation pulses comprising at least one pair of opposing polarity pulses including a positive polarity pulse and a negative polarity pulse each delivered according to a programmed pulse amplitude and a programmed pulse width, the pair of opposing polarity pulses having an imbalanced charge; and controlling the therapy delivery circuit to modify the nth pulse to reduce an accumulation of the imbalanced charge after the at least one pair of opposing polarity pulses.

4. The device of claim 3, wherein the control circuit is further configured to:

determine a value of n based on the imbalanced charge of each pair of one positive polarity pulse and one negative polarity pulse.

5. The device of claim 1, wherein the control circuit is configured to control the therapy delivery circuit to modify every nth pulse of the plurality of electrical stimulation pulses by reversing the polarity of the nth pulse.

6. The device of claim 1, wherein the control circuit is configured to control the therapy delivery circuit to modify every nth pulse of the plurality of the electrical stimulation pulses by adjusting at least one of a pulse amplitude or a pulse width.

7. The device of claim 1, further comprising a memory comprising a lookup table of pulse modifications, wherein the control circuit is configured to:

establish a modification of every nth pulse by retrieving the modification from the lookup table; and control the therapy delivery circuit to modify every nth pulse according to the established modification.

8. The device of claim 1, wherein the control circuit is configured to:

select an electrical stimulation pulse output configuration; and establish a modification of every nth pulse based on the selected electrical stimulation output configuration.

9. The device of claim 8, wherein:

the therapy delivery circuit comprises a first output circuit for generating and delivering electrical stimulation pulses and a second output circuit for generating and delivering electrical stimulation pulses; and the control circuit is configured to:

select the electrical stimulation pulse output configuration by selecting one of the first output circuit and the second output circuit to deliver the plurality of electrical stimulation pulses, and establish the modification of every nth pulse by establishing at least one of: a value of n, a polarity of the nth pulse, an amplitude of the nth pulse, or a width of the nth pulse.

10. The device of claim 1, wherein the control circuit is further configured to:

detect a change in an electrical stimulation pulse output condition; and change the charge balancing pulse in response to detecting the change in the electrical stimulation pulse output condition.

11. The device of claim 10, wherein the control circuit is configured to detect the change in the electrical stimulation output condition by detecting at least one of: a change in a cardiac pacing mode, a change in an electrode vector impedance, a change in a pulse amplitude of the plurality of electrical stimulation pulses, a change in a pulse width of the plurality of electrical stimulation pulses, or a change in a rate of the electrical stimulation pulses.

12. The device of claim 10, wherein the control circuit is configured to change the charge balancing pulse by adjusting at least one of: a value of n, a polarity of the nth pulse, a pulse amplitude of the nth pulse, or a pulse width of the nth pulse.

13. The device of claim 1, wherein the control circuit is further configured to:

modify every nth pulse using a first modification and modify every mth pulse of the plurality of electrical stimulation pulses using a second modification for reducing a charge imbalance remaining after the nth pulse.

14. The device of claim 1, further comprising a housing enclosing the therapy delivery circuit and the control circuit and coupleable to an extra-cardiovascular cardiac pacing lead carrying at least one of the electrodes.

15. The device of claim 1, wherein the therapy delivery circuit is configured to generate and deliver the electrical stimulation pulses as cardiac pacing pulses.

16. A method comprising:

delivering a plurality of electrical stimulation pulses comprising at least one first pulse having a first polarity and at least one second pulse having a second polarity opposing the first polarity, the at least one first pulse and the at least one second pulse of the plurality of electrical stimulation pulses being charge imbalanced pulses delivering a net electrical charge; and delivering a charge balancing pulse by modifying every nth pulse of the plurality of electrical stimulation pulses to reduce the net electrical charge delivered over the plurality of electrical stimulation pulses.

17. The method of claim 16, wherein delivering the plurality of electrical stimulation pulses comprises delivering the electrical stimulation pulses as alternating polarity pulses.

18. The method of claim 16, wherein:

delivering the plurality of electrical stimulation pulses comprises delivering at least one pair of opposing polarity pulses comprising a positive polarity pacing pulse and a negative polarity pacing pulse each delivered according to a programmed pulse amplitude and a programmed pulse width, the pair of opposing polarity pulses having an imbalanced charge, and modifying the nth pulse to reduce an accumulation of the imbalanced charge after the at least one pair of opposing polarity pulses.

19. The method of claim 18, further comprising:
determining a value of n based on a charge imbalance of each pair of one positive polarity pulse and one negative polarity pulse.

20. The method of claim 16, wherein modifying every nth pulse of the plurality of electrical stimulation pulses comprises reversing the polarity of the nth pulse.

21. The method of claim 16, wherein modifying every nth pulse of the plurality of electrical stimulation pulses comprises adjusting at least one of a pulse amplitude or a pulse width.

22. The method of claim 16, further comprising:
storing a lookup table of pulse modifications in a memory;
establishing a modification of every nth pulse by retrieving the modification from the lookup table; and
modifying every nth pulse according to the established modification.

23. The method of claim 16, further comprising:
selecting an electrical stimulation pulse output configuration; and
establishing a modification of every nth pulse based on the selected electrical stimulation pulse output configuration.

24. The method of claim 23, further comprising
selecting the electrical stimulation pulse output configuration by selecting one of a first output circuit and a second output circuit of a therapy delivery circuit of the medical device for delivering the plurality of electrical stimulation pulses, and
establishing the modification of every nth pulse by establishing at least one of: a value of n, a polarity of the nth pulse, an amplitude of the nth pulse, or a width of the nth pulse.

25. The method of claim 16, further comprising:
detecting a change in an electrical stimulation pulse output condition; and
changing the charge balancing pulse in response to detecting the change in the electrical stimulation pulse output condition.

26. The method of claim 25, further comprising detecting the change in the electrical stimulation pulse output condition by detecting at least one of: a change in a cardiac pacing mode, a change in an electrode vector impedance, a change in a pulse amplitude of the plurality of electrical stimulation pulses, a change in a pulse width of the plurality of electrical stimulation pulses, or a change in a rate of the electrical stimulation pulses.

27. The method of claim 25, further comprising changing the charge balancing pulse by adjusting at least one of: a value of n, a polarity of the nth pulse, a pulse amplitude of the nth pulse, or a pulse width of the nth pulse.

28. The method of claim 16, further comprising modifying every nth pulse using a first modification and modifying every mth pulse of the plurality of electrical stimulation pulses using a second modification for reducing a charge imbalance remaining after the nth pulse.

29. The method of claim 16, further comprising delivering the plurality of electrical stimulation pulses via at least one electrode carried by an extra-cardiovascular lead.

30. The method of claim 16, wherein delivering the electrical stimulation pulses comprises delivering cardiac pacing pulses.

31. A non-transitory computer-readable medium storing a set of instructions which when executed by a control circuit of a medical device, cause the medical device to:
deliver a plurality of electrical stimulation pulses comprising at least one first pulse having a first polarity and at least one second pulse having a second polarity opposing the first polarity, the at least one first pulse and the at least one second pulse of the plurality of electrical stimulation pulses being charge imbalanced pulses delivering a net electrical charge; and
deliver a charge balancing pulse by modifying every nth pulse of the plurality of electrical stimulation pulses to reduce the net electrical charge delivered over the plurality of electrical stimulation pulses.

\* \* \* \* \*